US008168777B2

(12) United States Patent
Millar et al.

(10) Patent No.: US 8,168,777 B2
(45) Date of Patent: *May 1, 2012

(54) BISULPHITE REAGENT TREATMENT OF NUCLEIC ACID

(75) Inventors: Douglas Spencer Millar, Revesby (AU); Cassandra Jean Vockler, Turramurra (AU); Neralie Ann Coulston, Avalon Beach (AU)

(73) Assignee: Human Genetic Signatures Pty. Ltd., New South Wales (AU)

(*) Notice: Subject to any disclaimer, the term of this patent is extended or adjusted under 35 U.S.C. 154(b) by 275 days.

This patent is subject to a terminal disclaimer.

(21) Appl. No.: 12/413,380

(22) Filed: Mar. 27, 2009

(65) Prior Publication Data

US 2009/0263909 A1   Oct. 22, 2009

Related U.S. Application Data

(63) Continuation-in-part of application No. 10/555,465, filed as application No. PCT/AU2004/000549 on Apr. 29, 2004, now abandoned.

(51) Int. Cl.
C07H 21/00 (2006.01)
C07H 21/04 (2006.01)

(52) U.S. Cl. ...................... 536/25.3; 536/23.1

(58) Field of Classification Search .................. None
See application file for complete search history.

(56) References Cited

U.S. PATENT DOCUMENTS

| | | | |
|---|---|---|---|
| 5,629,156 A | 5/1997 | Shah et al. | |
| 5,750,338 A | 5/1998 | Collins et al. | |
| 5,786,146 A | 7/1998 | Herman et al. | |
| 5,824,517 A | 10/1998 | Cleuziat et al. | |
| 5,952,174 A | 9/1999 | Nikiforov et al. | |
| 6,156,501 A | 12/2000 | McGall et al. | |
| 6,265,171 B1 | 7/2001 | Herman et al. | |
| 6,331,393 B1 | 12/2001 | Laird et al. | |
| 6,692,918 B2 | 2/2004 | Kurn | |
| 6,960,436 B2 | 11/2005 | Cottrell | |
| 7,008,770 B1 | 3/2006 | Berlin | |
| 7,288,373 B2* | 10/2007 | Millar et al. | 435/6 |
| 7,504,207 B2 | 3/2009 | Bergquist | |
| 2002/0086324 A1 | 7/2002 | Laird et al. | |
| 2002/0142397 A1 | 10/2002 | Collas et al. | |
| 2003/0073081 A1 | 4/2003 | Mukai et al. | |
| 2003/0119025 A1 | 6/2003 | Olek et al. | |
| 2003/0143577 A1 | 7/2003 | Hogrefe et al. | |
| 2004/0086944 A1 | 5/2004 | Grigg et al. | |
| 2004/0203004 A1 | 10/2004 | Bernard et al. | |
| 2004/0219539 A1 | 11/2004 | Millar et al. | |
| 2005/0019762 A1* | 1/2005 | Olek | 435/6 |
| 2005/0059003 A1 | 3/2005 | Enoki et al. | |
| 2005/0118578 A1 | 6/2005 | Mineno et al. | |
| 2005/0202490 A1 | 9/2005 | Makarov | |
| 2006/0014144 A1 | 1/2006 | Christensen et al. | |
| 2006/0051771 A1 | 3/2006 | Murphy et al. | |
| 2006/0166203 A1 | 7/2006 | Took | |
| 2007/0020633 A1 | 1/2007 | Millar | |
| 2007/0026070 A1 | 2/2007 | Vonwiller | |
| 2007/0042365 A1 | 2/2007 | Millar et al. | |
| 2007/0178457 A1 | 8/2007 | Millar | |
| 2007/0178459 A1 | 8/2007 | Millar | |
| 2007/0190530 A1 | 8/2007 | Birkner et al. | |
| 2007/0264653 A1 | 11/2007 | Berlin et al. | |
| 2008/0050738 A1 | 2/2008 | Millar | |
| 2009/0029346 A1 | 1/2009 | Millar et al. | |
| 2009/0042732 A1 | 2/2009 | Millar | |
| 2009/0130657 A1 | 5/2009 | Millar | |

FOREIGN PATENT DOCUMENTS

| | | |
|---|---|---|
| EP | 1 130 113 | 9/2001 |
| EP | 1 319 718 | 6/2003 |
| WO | WO 98/20157 | 5/1988 |
| WO | WO 95/01456 | 1/1995 |
| WO | WO 95/22623 | 8/1995 |
| WO | WO 97/41254 | 11/1997 |
| WO | WO 97/45559 | 12/1997 |
| WO | WO 98/29108 | 7/1998 |
| WO | WO 99/09211 A2 | 2/1999 |
| WO | WO 99/14226 | 3/1999 |
| WO | WO 99/49081 A2 | 9/1999 |
| WO | WO 00/44934 | 8/2000 |
| WO | WO 00/50869 A2 | 8/2000 |
| WO | WO 01/09374 A2 | 2/2001 |
| WO | WO 01/38565 A2 | 5/2001 |
| WO | WO 01/42493 A2 | 6/2001 |

(Continued)

OTHER PUBLICATIONS

Clark et al., High sensitivity mapping of methylated cytosines, Nucleic Acids Research, 1994, vol. 22, No. 15, 2990-2997.*

Wang et al., Comparison of bisulfite modification of 5-methyldeoxycytidine and deoxycytidine residues, Nucleic Acids Research, vol. 8 No. 20 1980, pp. 4777-4790.*

Herman et al., Unit 10.6 Methylation-Specific PCR, Current Protocols in Human Genetics, Published Online: May 1, 2001, pp. 10.6.1-10.6.10, DOI: 10.1002/0471142905.hg1006s16, Copyright © 2003 by John Wiley and Sons, Inc: http://onlinelibrary.wiley.com/doi/10.1002/0471142905.hg1006s16/full.*

Badal Sushma et al.: "The human papillomavirus-18 genome is efficiently targeted by cellular DNA methylation" Virology, vol. 324, No. 2, Jul. 1, 2004, pp. 483-492.

(Continued)

*Primary Examiner* — Mark Staples
(74) *Attorney, Agent, or Firm* — Knobbe Martens Olson & Bear LLP

(57) ABSTRACT

Methods for treating nucleic acid including: (a) providing an alkali environment to a nucleic acid sample; (b) reacting the nucleic acid sample with a bisulphite reagent and incubating the reaction so as to form a treated nucleic acid sample where methylated nucleotides in the nucleic acid sample remain unchanged while unmethylated nucleotides are converted to another form; (c) removing unwanted reagents or diluents from the treated nucleic acid sample; and (d) carrying out de-sulphonation of the precipitated treated nucleic acid at a temperature from 70° C. to 95° C. by adjusting the precipitated treated nucleic acid to a pH of between 10 and less than 12.5 to remove sulphonate groups present on the treated nucleic acid and obtain a nucleic acid sample substantially free of sulphonate groups.

24 Claims, 9 Drawing Sheets

FOREIGN PATENT DOCUMENTS

| | | |
|---|---|---|
| WO | WO 01/76451 A2 | 10/2001 |
| WO | WO 02/38801 | 5/2002 |
| WO | WO 02/46452 | 6/2002 |
| WO | WO 02 46452 A2 * | 6/2002 |
| WO | WO 02/072880 | 9/2002 |
| WO | WO 02/097065 | 12/2002 |
| WO | WO 03/008623 A2 | 1/2003 |
| WO | WO 03/048732 | 6/2003 |
| WO | WO 03/051901 A2 | 6/2003 |
| WO | WO 03/052132 A2 | 6/2003 |
| WO | WO 03/052133 A2 | 6/2003 |
| WO | WO 03/052134 A2 | 6/2003 |
| WO | WO 2004/015139 | 2/2004 |
| WO | WO 2004/065625 | 8/2004 |
| WO | WO 2004/090166 | 10/2004 |
| WO | WO 2004/096825 | 11/2004 |
| WO | WO 2004/111266 | 12/2004 |
| WO | WO 2005/021778 | 3/2005 |
| WO | WO 2005/056790 A1 | 6/2005 |
| WO | WO 2006/058393 | 6/2006 |
| WO | WO 2006/066353 | 6/2006 |

OTHER PUBLICATIONS

Badal V. et al.: "CpG methylation of human papillomavirus type 16 DNA in cervical cancer cell lines and in clinical specimens: Genomic hypomethylation correlates with carcinogenic progression" Journal of Virology, The American Society for Microbiology, US, vol. 77, No. 11, Jun. 1, 2003, pp. 6227-6234.
Baleriola C et al.: "Comparison of a novel HPV test with the Hybrid Capture II (hcII) and a reference PCR method shows high specificity and positive predictive value for 13 high-risk human papillomavirus infections" Journal of Clinical Virology, Elsevier, Amsterdam, NL, vol. 42, No. 1, May 1, 2008, pp. 22-26.
European Search Report issued in corresponding European Application No. 06774977, dated Jul. 28, 2009.
Extended European Search Report issued in corresponding European Application No. 05779000.8, dated Dec. 4, 2008.
Extended European Search Report issued in corresponding European Application No. 05821631.8, dated Nov. 7, 2008.
Feng et al: "Detection of hypermethylated genes in women with and without cervical neoplasia." Journal of the National Cancer Institute Feb. 16, 2005, vol. 97, No. 4, Feb. 16, 2005, pp. 273-282.
Gu W. et al, Depletion of *Saccharomyces cerevisiae* tRNAHis Guanylyltransferase Thglp leads to uncharged tRNAH is with additional m5C, Mol Cell Biol. Sep. 2005; vol. 25, No. 18, pp. 8191-8201.
International Preliminary Report on Patentability issued on the corresponding PCT Application No. PCT/AU2006/000698, dated Apr. 20, 2007.
International Search Report issued on corresponding PCT Application No. PCT/AU2006/000755, dated Aug. 30, 2006.
International Search Report issued on corresponding PCT Application No. PCT/AU2008/000367, dated May 14, 2008.
International Search Report Issued on the corresponding PCT Application No. PCT/AU2006/000698, dated Aug. 1, 2006.
Kalantari, Mina et al. "Conserved methylation patterns of human papillomavirus type 16 DNA in asymptomatic infection and cervical neoplasia," Journal of Virology, vol. 78, No. 23, Dec. 2004, pp. 12762-12772.
Kim T Y et al: "DNA hypermethylation in gastric cancer" Alimentary Pharmacology & Therapeutics, vol. 20, No. Suppl. 1, Jul. 2004, pp. 131-142.
Kozak et al.: "Influence of secondary structure on binding and migration of 40S ribosomal subunits," Cell, vol. 19, 1980, pp. 79-90.
Malyukova A V et al: "Methylation of the Putative Tumor Suppressor Gene RASSF1A in Primary Cervical Tumors" Molecular Biology, Kluwer Academic Publishers-Plenum Publishers, NE, vol. 38, No. 6, Nov. 1, 2004, pp. 857-864.
Narayan, Gopeshwar et al: "Frequent Promoter Methylation of CDH1, DAPK, RARB, and HIC1 Genes in Carcinoma of Cervix Uteri: Its Relationship to Clinical Outcome" Molecular Cancer, Biomed Central, London, GB, vol. 2, No. 1, May 13, 2003, p. 24.
Nilsson et al. Science. 265:2085-2088 (1994).
Nousbaum, J. et al., "Prospective Characteristics of Full-Length Hepatitis C Virus NS5A Quasispecies during Induction and Combination Antiviral Therapy," Journal of Virology, 74, No. 19, pp. 9028-9038 (2000).
Office Action in U.S. Appl. No. 10/543,017 dated Dec. 8, 2008.
Office Action in U.S. Appl. No. 10/543,017 dated Jun. 20, 2008.
Office Action in U.S. Appl. No. 10/543,017 dated Oct. 19, 2007.
Office Action in U.S. Appl. No. 11/573,873 dated May 4, 2009.
Office Action in U.S. Appl. No. 11/573,873 dated Sep. 2, 2009.
Office Action in U.S. Appl. No. 11/660,586 dated Sep. 15, 2009.
Ratushna V.G. et al.: "Secondary structure in the target as a confounding factor in synthetic oligomer microarray design," BMC Genomics, vol. 6, No. 1, Mar. 2005, p. 31.
Supplementary European Search Report issued on corresponding European Patent Application No. EP 05 81 3335, dated Mar. 12, 2009.
Supplementary European Search Report issued on corresponding European Patent Application No. EP 06 77 4977, dated Jul. 28, 2009.
Ushijima Toshikazu et al: "Aberrant methylations in cancer cells: Where do they come from?" Cancer Science, vol. 96, No. 4, Apr. 2005, pp. 206-211.
Verma M: "Viral Genes and Methylation" Annals of the New York Academy of Sciences 200303 US, vol. 983, Mar. 2003, pp. 170-180.
Widschwendter et al.: "Analysis of Aberrant DNA Methylation and Human Papillomavirus DNA in Cervicovaginal Specimens to Detect Invasive Cervical Cancer and Its Precursors" Clinical Cancer Research, The American Association for Cancer Research, US, vol. 10, No. 10, May 15, 2004, pp. 3396-3400.
Yanagi et al., "Hepatitis C Virus: An Infectious Molecular Clone of a Second Major Genotype (2A) and Lack of Viability of Intertypic 1A and 2A Chimeras," Virology 262, p. 250-263 (1999).
Zeschnig k et al., "A novel real-time PCR assay for quantitative analysis of methylated alleles (QAMA): analysis of the retinoblastoma locus," Nucleic Acid Research 2004, vol. 32, No. 16, pp. 1-5.
Clark, et al., "Bisulphite genomic sequencing of methylated cytosines." Laboratory Methods for the Detection of Mutations and Polymorphisms in DNA. Graham R. Taylor, Ed. CRC Press, New York (1997), pp. 151-162.
Dean et al., "Comprehensive human genomeamplification using multiple displacement amplification." PNAS, 99(8): 5261-5266 (2002).
Eads et al., "MethylLight: a high-throughput assay to measure DNA methylation." Nucleic Acids Research, 28(8): i-viii (2000).
Feil, et al. "Methylation analysis on individual chromosomes: improved protocol for bisulphate genomic sequencing." (1994) Nucleic Acids Research 22(4): 695-696.
Frommer et al. "A genomic sequencing protocol that yields a positive display of 5-methylcytosine residues in individual DNA strands." *Proc. Natl. Acad. Sci.* 89:1827-1831.
Grigoriev et al., "A Triple Helix-forming Oligonucleotide-Intercalator Conjugate Acts as a Transcriptional Repressor via Inhibition of NFkB Binding to Interleukin-2 Receptor a-Regulatory Sequence." The Journal of Biological Chemistry, 267 (5): 3389-3395 (1992).
Grunau, et al. "Bisulfite genomic sequencing: systematic investigation of critical experimental parameters." Nucleic Acids Research, (2001), vol. 29, No. 13e65. pp. 1-7.
Hakelien et al., "Reprogramming fibroblasts to express T-cell functions using cell extracts." Nature Briotechnology, 20(5): 460-466 (2002).
Hakelien et al., "Novel Approaches to Transdifferentiation", Cloning and Stem Cells, 4: 379-387 (2002).
Herman et al. "Methylation-specific PCR: A novel PCR assay for methylation status of CpG islands." *Proc. Natl. Acad. Sci. USA.* 93:9821-9826 (1996).
Hosono et al. "Unbiased Whole-Genome Amplification Directly from Clinical Samples." *Genome Research*; 13:954-964 (2003).
International Human Genome Sequencing Consortium. "Initial sequencing and analysis of the human genome." *Nature.* 409(6822):860-921 (2001).
Kinoshita et al., "Methylation of the androgen receptor minimal promoter silences transcription in human prostate cancer." Cancer Research, 60(13): 3623-3630 (Jul. 1, 2000).

Kono, "Nuclear transfer and reprogramming." Reviews of Reproduction, Journal of Reproduction and Fertility, vol. 2 No. 2, pp. 74-80 (May 1997).

Millar et al. "A distinct sequence (ATAAA)n separates methylated and unmethylated domains at the 5'-end of the GSPTI CpG island." *J. Biol. Chem.* 275(32):24893-24899 (2000).

Millar et al. "Detailed methylation analysis of the glutathione S-transferase pi (GSPTI) gene in prostate cancer." *Oncogene.* 18(6):1313-1324 (1999).

Monk, "Epigentic programming of differential gene expression in development and evolution" Dev. Genetics, vol. 17, pp. 183-197 (1995).

Newton et al., "The production of PCR products with 5' single-stranded tails using primers that incorporate novel phosphoramidite intermediates." Nucleic Acid Res. vol. 21 No. 5, pp. 1155-1162 (1993).

Venter et al. "The sequence of the human genome." *Science.* 292(5523):1304-1351 (2001).

Waranecke et al., "Detection and measurement of PCR bias in quantitative methylation analysis of bisulphite-treated DNA," Nucleic Acids Research, vol. 25 No. 21, pp. 4422-4426, (1997).

Xiong, et al. "COBRA: a sensitive and quantitative DNA methylation assay." (1997) Nucleic Acids Research, 25 (12): 2532-2534.

Database Accession No. M24485.

Specification and Preliminary Amendment from co-pending U.S. Appl. No. 10/555,465, filed Aug. 28, 2006.

Office Action in U.S. Appl. No. 11/660,586 dated Aug. 6, 2010.

Office Action in U.S. Appl. No. 11/660,586 dated Jul. 20, 2011.

Christensen et al., "Intercalating nucleic acids containing insertions of 1-o-(1-pyrenylmethyl)glycerol: stabilization of dsDNA and discrimination of DNA over RNA." Nucleic Acid Res. vol. 30, No. 22, pp. 4918-4925, (2002).

Clark et al. "High sensitivity mapping of methylated cytosines." *Nucleic Acids Research.* 22(15):2990-2997 (1994).

Nilsson et al., "Padlock Probes: Circularizing Olignucleotides for Localized DNA Detection", Science; 265:2085-2088 (1994).

Office Action in U.S. Appl. No. 10/428,310 dated Aug. 31, 2006.

Office Action in U.S. Appl. No. 10/428,310 dated Jan. 4, 2006.

Office Action in U.S. Appl. No. 10/428,310 dated Jul. 5, 2006.

Office Action in U.S. Appl. No. 10/428,310 dated Nov. 3, 2006.

Office Action in U.S. Appl. No. 10/416,637 dated May 4, 2006.

Office Action in U.S. Appl. No. 10/536,633 dated Apr. 4, 2007.

Office Action in U.S. Appl. No. 10/536,633 dated Jan. 25, 2007.

Okada, et al. "Sequence Determination of Rat U5 RNA Using a Chemical Modification Procedure for Counteracting Sequence Compression." (1982) J. Biochem. 91: 1281-1291.

Olek et al. "A modified and improved method for bisulphate based cytosine methylation analysis." *Nucleic Acids Research.* 24(24):5064-5066 (1996).

Paulin et al., "Urea improves efficiency of bisulphite-mediated sequencing of 5'-methylcytosine in genomic DNA." Nucleic Acid Research, 26(21): 5009-5010 (Nov. 1, 1998).

Pietrobono et al., "Quantitative analysis of DNA demethylation and transcriptional reactivation of the FMR1 gene in fragile X cellstreated with 5-azadeoxycytidine." Nucleic Acids Research, 30(14): 3278-3285 (2002).

Rein et al., "Identifying 5-methylcytosine and related modifications in DNA genomes." Nucleic Acids Research, 26 (10): 2255-2264 (May 15, 1998).

Raizis et al. *Anal. Biochem.* 226:161-166 (1995).

Robertson et al. *Blood.* 90:4480-4484 (1997).

Robertson et al. "DNA methylation: past, present, and future directions." Carcinogenesis. 21(3): 461-467 (2000).

Sakaguchi et al. "Cautionary Note on the Use of dUMP-Containing PCR Primers with *Pfu* and Vent$_R$® DNA Polymerases." *Biotechniques*; 21(3):368 & 370 (1996).

Sakashita et al., "Dynamic DNA methylation change in the CpG island region of p15 during human myeloid development", J. Clin. Invest., 108: 1195-1204 (2001).

Shapiro et al. "Deamination of cytosine derivatives by bisulfite. Mechanism of the reaction." *J. Am. Chem. Soc.* 96:206-212 (1974).

Tada et al., "Embryonic germ cells induce epigenetic reprogramming of somatic nucleus in hybrid cells." The EMBO Journal, 16(21): 6510-6520 (1997).

Telenius et al. "Degenerate Oligonucleotide-Primed PCR: General Amplification of Target DNA by a Single Degenerate Primer." *Genomics*; 13(3):718-725 (1992).

Tohgi et al. *Molecular Brain Research.* 65:124-128 (1999).

Pending claims in U.S. Appl. No. 11/660,586 on Jul. 29, 2011.

Pending claims in U.S. Appl. No. 12/892,484 on Jul. 29, 2011.

Pending claims in U.S. Appl. No. 12/066,644 on Jul. 29, 2011.

Pending claims in U.S. Appl. No. 12/744,310 on Jul. 29, 2011.

Pending claims in U.S. Appl. No. 12/744,305 on Jul. 29, 2011.

Pending in for U.S. Appl. No. 12/747,483 on Jul. 29, 2011.

Pending claims in U.S. Appl. No. 12/531,482 on Jul. 29, 2011.

Office Action in U.S. Appl. No. 11/660,586 dated Aug. 6, 2010, Our Ref.

Office Action in U.S. Appl. No. 11/660,586 dated Jul. 20, 2011, Our Ref.

\* cited by examiner

Figure 1

Figure 1. HGS method verus traditional bisulphite method (Clark et al 1994)

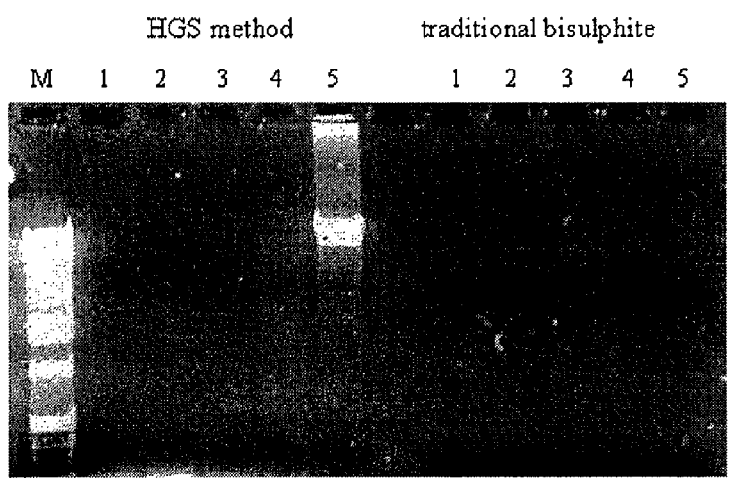

1. DNA extracted from 2 LNCaP cells and treated with bisulphite
2. DNA extracted from 20 LNCaP cells and treated with bisulphite
3. DNA extracted from 200 LNCaP cells and treated with bisulphite
4. DNA extracted from 2,000 LNCaP cells and treated with bisulphite
5. DNA extracted from 20,000 LNCaP cells and treated with bisulphite

Figure 5
Bisulphite treated RNA
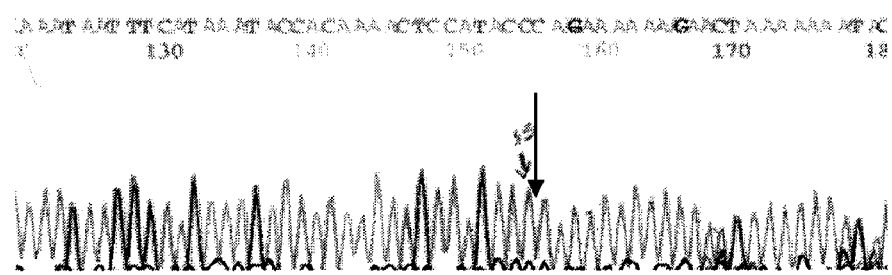
Wild type RNA
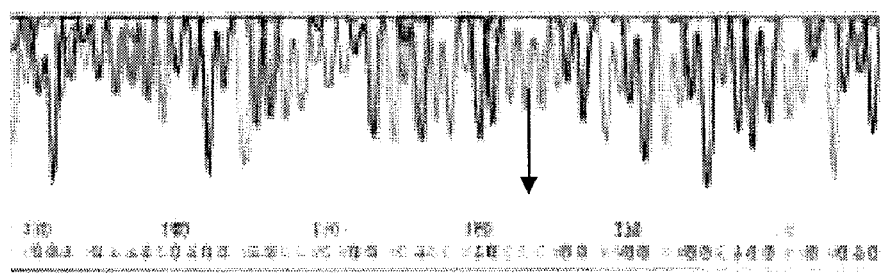

SEQUENCE LISTING

<160> NUMBER OF SEQ ID NOS: 8

<210> SEQ ID NO 1
<211> LENGTH: 27
<212> TYPE: DNA
<213> ORGANISM: Homo sapien

<400> SEQUENCE: 1

```
tttgttgttt gtttatttttt taggttt                                27

<210> SEQ ID NO 2
<211> LENGTH: 26
<212> TYPE: DNA
<213> ORGANISM: Homo sapien

<400> SEQUENCE: 2
aacctaatac taccaattaa ccccat                                  26

<210> SEQ ID NO 3
<211> LENGTH: 29
<212> TYPE: DNA
<213> ORGANISM: Homo sapien

<400> SEQUENCE: 3
gggatttggg aaagagggaa aggtttttt                               29

<210> SEQ ID NO 4
<211> LENGTH: 26
<212> TYPE: DNA
<213> ORGANISM: Homo sapien

<400> SEQUENCE: 4
actaaaaact ctaaaaaccc catccc                                  26

<210> SEQ ID NO 5
<211> LENGTH: 25
<212> TYPE: DNA
<213> ORGANISM: Homo sapien

<400> SEQUENCE: 5
ttaatatttt agttatgtat gttgt                                   25

<210> SEQ ID NO 6
<211> LENGTH: 22
<212> TYPE: DNA
<213> ORGANISM: Homo sapien

<400> SEQUENCE: 6
cttcattata ctaaatacca aa                                      22

<210> SEQ ID NO 7
<211> LENGTH: 25
<212> TYPE: DNA
<213> ORGANISM: Homo sapien

<400> SEQUENCE: 7
tcaacacccc agccatgtac gttgc                                   25

<210> SEQ ID NO 8
<211> LENGTH: 22
<212> TYPE: DNA
<213> ORGANISM: Homo sapien

<400> SEQUENCE: 8
gatcttcatt gtgctgggtg cc                                      22
```

BISULPHITE REAGENT TREATMENT OF NUCLEIC ACID

RELATED APPLICATIONS

This application is a continuation-in-part of U.S. application Ser. No. 10/555,465, filed Aug. 28, 2006 (abandoned), which is the US National Phase filing under 35 U.S.C. §371 of PCT/AU2004/000549, filed Apr. 29, 2004, entitled "TREATMENT OF NUCLEIC ACID", which designated the United States and was published in English on Nov. 11, 2004, and which claims priority to U.S. application Ser. No. 10/428,310, filed May 2, 2003 (now U.S. Pat. No. 7,288,373, issued Oct. 30, 2007), the entire content of which is incorporated herein by reference.

FIELD OF THE INVENTION

The present invention relates to modified methods for treating nucleic acid, particularly methylated nucleic acid using bisulphite.

BACKGROUND OF THE INVENTION

As a result of advances in automated sequencing technology, much work has been carried out on determining coding regions of DNA resulting in the full sequencing of many animal genomes including the human genome. It has been realised for many years that the majority of genomic DNA, however, is non-coding and this material was once considered as "junk" DNA. Analysis of the non-coding regions of DNA is now being considered as important in the study of gene expression and function. Methylation states or patterns in nucleic acid, particularly genomic DNA, is thought to have a functional or regulatory role in gene expression and control in animals.

It has been demonstrated that, in single stranded DNA, sodium bisulphite preferentially deaminates cytosine to uracil, compared to a very slow rate of deamination of 5-methylcytosine to thymine (Shapiro, R, DiFate, V., and Welcher, M, (1974) J. Am. Chem. Soc. 96: 906-912). This observation served as the basis for the development of the bisulphite genomic sequencing protocol of Frommer et al 1992 [Frommer M, McDonald L E, Millar D S, Collis C M, Watt F, Grigg G W, Molloy P L and Paul C L. PNAS 89: 1827-1831 (1992), which is incorporated herein by reference]. In summary, this method as presently practiced involves the following general steps: alkaline denaturation of DNA; deamination using sodium bisulphite; de-sulphonation by desalting followed by sodium hydroxide treatment; neutralization and desalting.

One of the major disadvantages of the bisulphite modification procedure and the established variation thereof is that it has been shown that the procedure results in the degradation of between 84-96% of the original input DNA (Grunau et al. Nucleic Acids Research 29 (13) e65; (2001). The high loss associated with the procedure means that practically it is very difficult to successfully analyse small numbers of cells for their methylation status, or successfully analyse ancient archival specimens in which the DNA is already in a partially degraded state. In addition, due to inherent degradation of the current methods, it is not possible to sequence and assemble the complete genome of an organism to determine its genome-wide methylation profile in the same manner as has been successfully applied by the public Human Genome Project (International Human Genome Sequencing Consortium, 2001, Nature, 409, 860-921) or the private CELERA sequencing project (J Craig Venter et al., 2001, Science, 291, 1304-1351) as the DNA would be so fragmented as it would not be able to be cloned, sequenced, and assembled in any meaningful way owing to the huge number of "gaps" in the sequence.

A further disadvantage with the bisulphite method as presently practiced is that, in general, only small fragments of DNA can be amplified. Experience shows that generally less than about 500 base pairs (bp) can be successfully treated and amplified. The present technique is not applicable to new molecular biological methods such as Long Distance polymerase chain reaction (PCR) which has made it possible to amplify large regions of untreated genomic DNA, generally up to about 50 kb. At present, it is not even possible to analyse the methylation status of intact genes, as a large number of genes in mammalian genomes exceed 50 kb in length.

To look at the methylation status of even relatively small genes (<4 kb), PCR reactions have had to be staggered across the gene region of interest (D. S Millar, K. K Ow, C. L. Paul, P. J. Russell, P. L. Molloy, S. J. Clark, 1999, *Oncogene*, 18(6):1313-24; Millar D S, Paul C L, Molloy P L, Clark S J. (2000), J Biol Chem; 275(32):24893-9). The methods presently used for bisulphite DNA treatment have also been laborious and time consuming. Standard methods typically require multiple tube changes, column purifications, dialysis, embedding the DNA in agarose beads or the addition of additives to the reaction in an attempt to reduce problems such as non-conversion of certain regions of genomic DNA. Thus a more reliable method that does not lead to substantial DNA degradation, and which overcomes or at least reduces the multiple problems associated with present DNA treatment, is required.

SUMMARY OF THE INVENTION

The present invention relates to an improved bisulphite treatment method of nucleic acids which is efficient, adaptable for use with many different molecular biological techniques, and can achieve significant retention of nucleic acid, which is herein termed the Human Genetic Signatures (HGS) bisulphite method or the method of present invention.

The invention provides, in one embodiment, a method for treating nucleic acids. The method can include the steps of denaturing a nucleic acid sample; incubating the nucleic acid sample with a bisulphite reagent, thereby modifying unmethylated nucleotides with sulphonate groups; removing any unwanted reagents from the treated nucleic acid; and reacting the modified nucleic acid sample to remove sulphonate groups. The denaturation of the nucleic acid can be performed, for example, by treatment with alkali.

In another embodiment, the present invention provides a method for treating nucleic acid comprising:

(a) providing a denaturing environment to a nucleic acid sample;

(b) reacting the nucleic acid sample with a bisulphite reagent and incubating the reaction so as to form a treated nucleic acid sample;

(c) substantially removing unwanted reagents or diluents from the treated nucleic acid sample; and (d) carrying out de-sulphonation of the treated nucleic acid so as to remove sulphonate groups present on the treated nucleic acid so as to obtain a nucleic acid sample substantially free of sulphonate groups without inducing significant amounts of strand breakage.

Preferably, the reacting step (b) results in any methylated nucleotides in the nucleic acid sample remaining unchanged while unmethylated nucleotides are converted to another form.

The method typically retains more than about 50%, generally more than about 75%, and can be more than about 95% of the starting nucleic acid in the sample. The methods of the invention can be carried out without causing any substantial degradation or loss of the nucleic acid sample. In contrast, bisulphite methods presently in use or described in the prior art typically result in loss of up to about 96% of the nucleic acid sample so that only about 4% of the nucleic acid is actually available for analysis.

The method may further comprise:
(e) further processing or analysing the treated nucleic acid sample.

The sample may include DNA or RNA or a combination of both DNA and RNA.

Unlike prior art methods, there is no need to completely separate or isolate the treated nucleic acid from the bisulphite reagent. There is no need to employ chromatography separation methods, for example, as presently required by prior art methods. The dilution step according to the present invention assists in minimizing loss of sample.

The present invention also relates to kits containing reagents and instructions to carry out the method according to the present invention.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred embodiments will be described with reference to the following drawings and examples.

BRIEF DESCRIPTION OF THE DRAWINGS

FIG. 1 shows comparison of recovery of bisulphite-treated DNA from various tissue samples between the HGS bisulphite method and traditional bisulphite method (Clark et al., (1994) Nucleic Acids Res. 22:2990-2997). Well #1, DNA extracted from 2 LNCaP cells and treated with bisulphite; Well #2, DNA extracted from 20 LNCaP cells and treated with bisulphite; Well #3, DNA extracted from 200 LNCaP cells and treated with bisulphite; Well #4, DNA extracted from 2,000 LNCaP cells and treated with bisulphite; and Well #5, DNA extracted from 20,000 LNCaP cells and treated with bisulphite. The HGS method is shown on the left (lanes marked 1-5, respectively, as indicated above); the traditional bisulphite method is shown on the right (lanes marked 1-5, respectively, as indicated above).

FIG. 5 shows confirmation that the PCR products generated in FIG. 4 were derived from the bisulphite treated genomic RNA. The arrow shows the splice site between exon 3 and 4 in the human beta-actin transcript.

Lane 2 2000 cell equivalent (starting volume in the bisulphite modification)

Lane 3 1000 cell equivalent (starting volume in the bisulphite modification)

Lane 4 400 cell equivalent (starting volume in the bisulphite modification)

Lane 5 200 cell equivalent (starting volume in the bisulphite modification)

Lane 6 0 cell equivalent (starting volume in the bisulphite modification)

Lane M HYPER LADDER® IV molecular weight marker (Bioline) NTC not shown but was clean.

Figure 10:
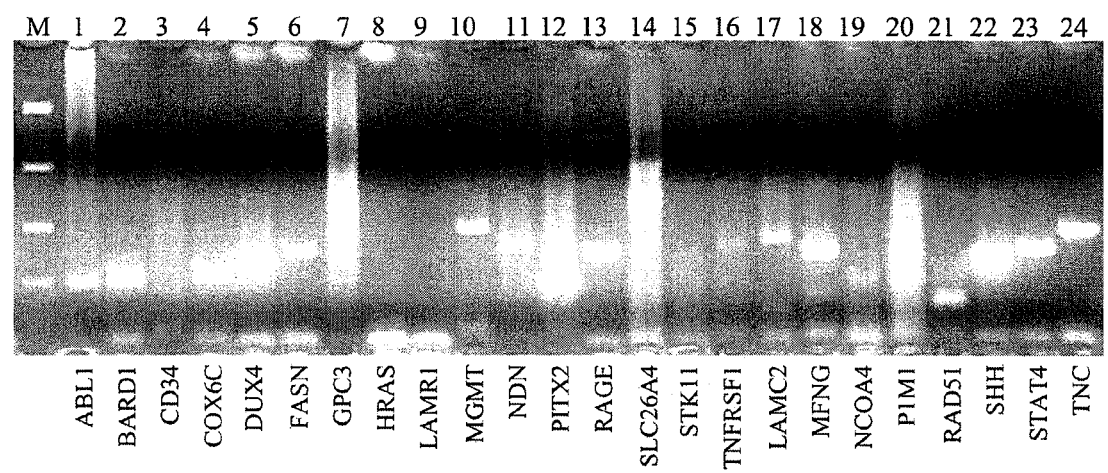

FIG. 10 shows PCR detection of human genomic DNA after using columns to remove the bisulphite and purify the converted DNA. The genomic locus that was amplified is named under each well.

Figure 11:
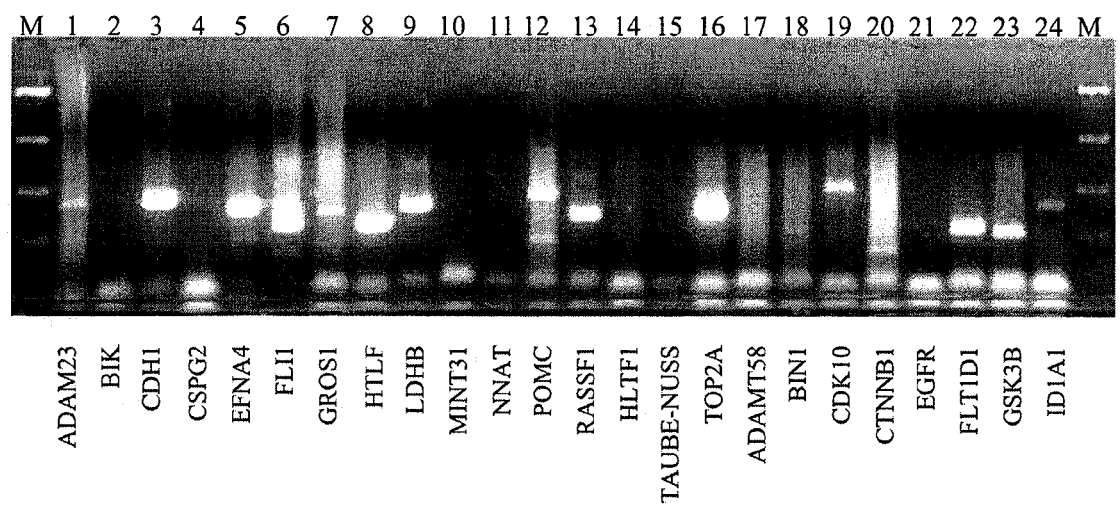

FIG. 11 shows PCR detection of human genomic DNA after using columns to remove the bisulphite and purify the converted DNA. The genomic locus that was amplified is named under each well.

Figure 12:
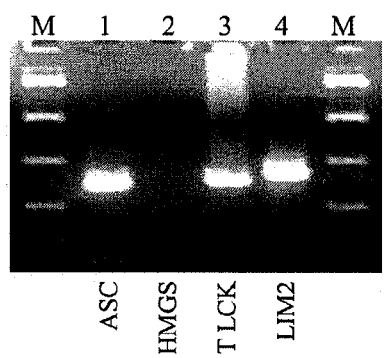

FIG. 12 shows PCR detection of very low amounts of human genomic DNA after using columns to remove the bisulphite and purify the converted DNA. Only 20 pg was seeded into each PCR (approximately 4 cell equivalents). The genomic locus that was amplified is named under each well.

Figure 13:
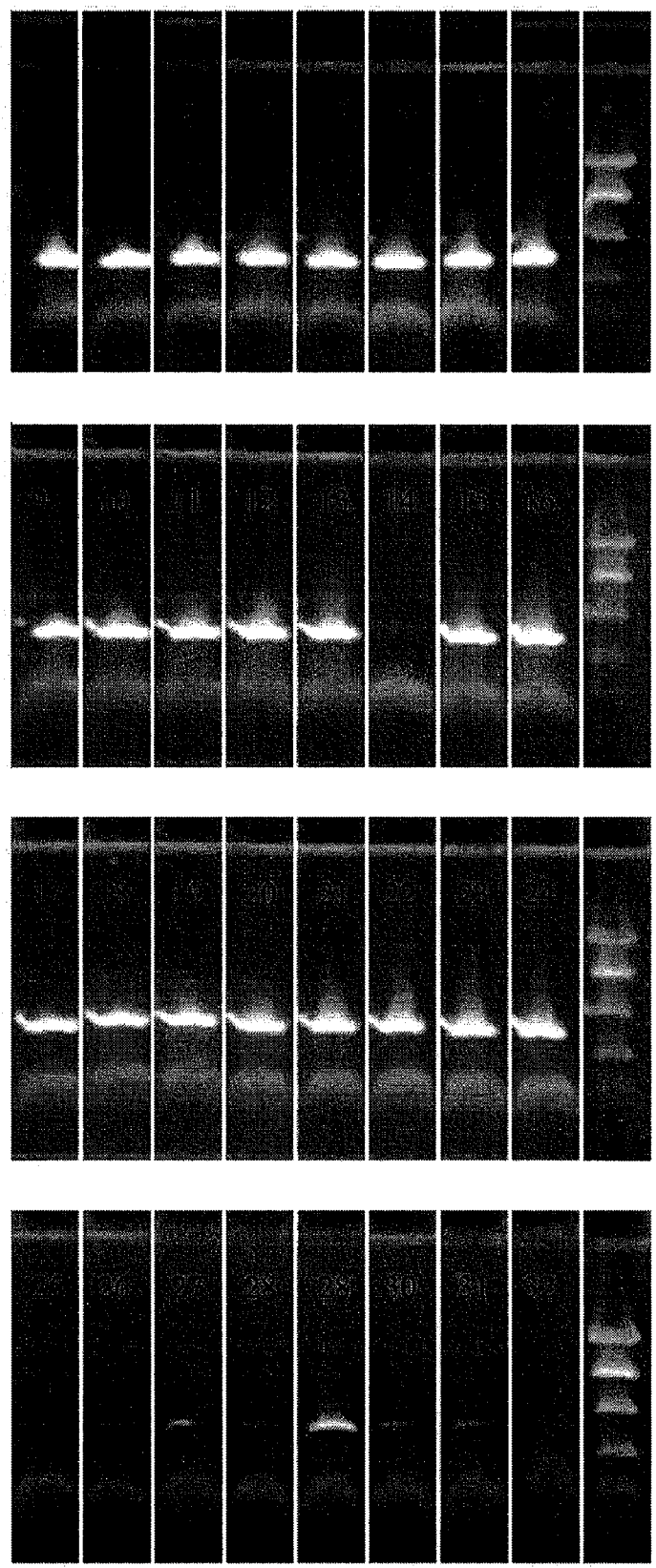

FIG. 13 shows detection of human genomic DNA using 96 well purification plates to remove the bisulphite and purify the converted DNA. Lanes 1-8; replicates of 1 µg/well, lanes 9-16 replicates of 100 ng/well, lanes 17-24; replicates of 25 ng/well, lanes 17-24; replicates of 1 ng/well.

DETAILED DESCRIPTION OF THE PREFERRED EMBODIMENT

Embodiments for treating nucleic acid are described in non-limiting detail below.

The invention provides methods for the treatment and analysis of nucleic acids. The methods are advantageous in that they provide a simple and highly efficient method for modification of nucleic acids and can be used, for example, to examine the methylation pattern or changes in methylation of genomic DNA or RNA, or detect groups of microorganisms that have become more similar after bisulphite conversion. The methods of the invention provide a simplified procedure with higher yields and higher molecular weight nucleic acid molecules relative to previously known methods, thus allowing the analysis of smaller amounts of nucleic acids as well as easy application to a large number of samples.

The invention provides a method for treating nucleic acid comprising:
(a) denaturing a nucleic acid sample;
(b) reacting the nucleic acid sample with a bisulphite reagent and incubating the reaction so as to form a treated nucleic acid sample;
(c) substantially removing unwanted reagents or diluents from the treated nucleic acid sample; and
(e) carrying out de-sulphonation of the treated nucleic acid so as to remove sulphonate groups present on the treated nucleic acid so as to obtain a nucleic acid sample substantially free of sulphonate groups.

In another embodiment, the invention provides a method for treating nucleic acid comprising:
(a) providing an alkali environment to a nucleic acid sample;
(b) reacting the nucleic acid sample with a bisulphite reagent and incubating the reaction so as to form a treated nucleic acid sample;
(c) substantially removing unwanted reagents or diluents from the treated nucleic acid sample; and
(d) carrying out de-sulphonation of the treated nucleic acid at a temperature from 70° C. to 95° C. by adjusting the treated nucleic acid to a pH of between 10 and less than 12.5 to remove sulphonate groups present on the treated nucleic acid and obtain a nucleic acid sample substantially free of sulphonate groups.

Preferably, the reacting step (b) results in any methylated nucleotides in the nucleic acid sample remaining unchanged while unmethylated nucleotides are converted to another form.

The denaturation of the nucleic acid sample can be performed, for example, by providing an alkali environment to a DNA sample. The methods are particularly useful in the analysis of DNA nucleic acid samples. The denaturation of RNA samples can be carried out by heating the RNA to resolve secondary structure. Heating typically is up to about 95° C., preferably between about 50° C. to 70° C. It will be appreciated, however, that the temperature is selected to preferably denature the RNA to remove secondary structure but not destroy or disrupt the RNA molecule.

Step (c) can be carried out by any suitable means such as precipitation, by immobilising the treated nucleic acid sample to a solid support and washing unwanted reagents or diluents from the immobilized treated nucleic acid sample.

Preferably, the solid support is glass, silica or ion-exchange media. The solid support can be provided or used as a column or beads or magnetic beads and the treated nucleic acid sample is eluted from the solid support prior to step (d).

The de-sulphonation step is generally carried out under controlled conditions so as to remove sulphonate groups present on the treated nucleic acid sample. The methods are advantageous because they can be performed so that the nucleic acid sample, for example, strands of DNA, are not broken or sheared to a significant extent. Such methods are particularly advantageous for RNA samples as addition of alkali as described in the traditional bisulphite procedure would result in total RNA degradation.

The invention thus provides, in one embodiment, a method for treating nucleic acids. The method can include the steps of denaturing a nucleic acid sample; incubating the nucleic acid sample with a bisulphite reagent, thereby modifying methylated nucleotides with sulphonate groups; diluting the modified nucleic acid sample; precipitating the modified nucleic acid sample; and reacting the modified nucleic acid sample to remove sulphonate groups. The denaturation of the nucleic acid can be performed, for example, by treatment with alkali, heating, or addition of other chemical or protein reagents that result in the formation of single stranded nucleic acids.

The method typically results in more than about 50%, generally more than about 75%, and can result in more than about 95% of the starting nucleic acid in the sample being retained. The present inventors have found that the method can be carried out without causing any substantial degradation or loss of the nucleic acid sample. In contrast, bisulphite methods presently in use or described in the prior art typically result in loss of up to about 96% of the nucleic acid sample.

The method may further comprise:
(f) processing or analysing the treated nucleic acid sample.

The sample may include DNA or RNA or a combination of both DNA and RNA.

The sample can be prepared from tissue, cells or can be any biological sample such as blood, urine, feces, semen, cerebrospinal fluid, lavage, cells or tissue from sources such as brain, colon, urogenital, lung, renal, hematopoietic, breast, thymus, testis, ovary, uterus, tissues from embryonic or extra-embryonic lineages, environmental samples, plants, microorganisms including bacteria, intracellular parasites virus, fungi, protozoan, viroid and the like. The best described mammalian cell types suitable for treatment by the present invention are summarized in B. Alberts et al., 1989, The Molecular Biology of the Cell, $2^{nd}$ Edition, Garland Publishing Inc New York and London, pp 995-997.

The analysis of 5-methyl cytosine residues in DNA or RNA from samples of human, animal, plant, bacterial, and viral origin is meant to cover all life cycle stages, in all cells, tissues and organs from fertilization until 48 hours post mortem, as well as samples that may be derived from histological sources, such as microscope slides, samples embedded in blocks, bodily fluids or samples extracted from synthetic or natural surfaces or from liquids.

The analyses are meant to include the naturally occurring variation between cells, tissues and organs of healthy individuals, (health as defined by the WHO), as well as cells, tissues and organs from diseased individuals. Diseased in this sense includes all human diseases, afflictions, ailments and deviant conditions described or referred to in Harrison's Principles of Internal Medicine, 12th Edition, edited by Jean D Wilson et al., McGraw Hill Inc, and subsequent later editions; as well as all diseases, afflictions ailments and deviant conditions described in OMIM (Online Mendelian Inheritance in Man, www.ncbi.gov), but with emphases on the leading causes of death, namely, malignant neoplasms, (cancer), ischaemic heart disease, cerebrovascular disease, chronic obstructive pulmonary disease, pneumonia and influenza, diseases of arteries, (including atherosclerosis and aortic aneurysm), diabetes mellitus, and central nervous system diseases, together with socially debilitating conditions such as anxiety, stress related neuropsychiatric conditions and obesity, and all conditions arising from abnormal chromosome number or chromosome rearrangements, (aneuploidy involving autosomes as well as sex chromosomes, duplications, deficiencies, translocations and insertions), as well as similar abnormalities of the mitochondrial genomes.

The normal or diseased individuals may be from (i) populations of diverse ethnicity and evolutionary lineages; (ii) strains and geographical isolates; (iii) sub species; (iv) twins or higher order multiplets of the same or different sex; (v) individuals arising from normal methods of conjugation, artificial insemination, cloning by embryonic stem cell methods, or by nuclear transfer, (from somatic or germ line nuclei), or from the input or modification of mitochondrial or other cellular organelles; (vi) individuals deriving from transgenic knock-out, knock-in or knock-down methods, (either in vivo, ex vivo, or by any method in which gene activity is transiently or permanently altered, e.g., by RNAi, ribozyme, transposon activation, drug or small molecule methodologies, Peptide Nucleic Acid (PNA), Intercalating Nucleic Acid (INA), Altritol Nucleic Acid (ANA), Hexitol Nucleic Acid (HNA), Locked Nucleic Acid (LNA), Cyclohexanyl Nucleic Acid (CNA), and the like, or nucleic acid based conjugates, including but not restricted to Trojan peptides, or individuals at any stages of pregnancy, normal or ectopic.

The analyses also include 5-methyl cytosine residues in DNA or RNA from prokaryotic or eukaryotic organisms and viruses (or combinations thereof), that are associated with human diseases in extracellular or intracellular modes, for the purposes of determining, and therapeutically altering, in both normally varying and diseased systems, the changed parameters and underlying mechanisms of:

(I) genetic diseases;

(II) non-genetic or epigenetic diseases caused by environmentally induced factors, be they of biological or non-biological origin, (environmental in this sense being taken to also include the environment within the organism itself, during all stages of pregnancy, or under conditions of fertility and infertility treatments);

(III) predisposition to genetic or non genetic diseases, including effects brought about by the "prion" class of factors, by exposure to pressure changes and weightlessness, or by radiation effects;

(IV) 5-methyl cytosine changes in the processes of aging in all cell types, tissues, organ systems and biological networks, including age related depression, pain, neuropsychiatric and neurodegenerative conditions and pre- and post-menopausal conditions, (including reduced fertility; in both sexes);

(V) 5-methyl cytosine changes in cancer, (including changes in cells with abnormal karyotypes arising from DNA amplification, deletion, rearrangement, translocation and insertion events), and their variations or alterations in different cell cycle phenomena (including cell cycle effects on diurnal rhythms, photoperiod, sleep, memory, and "jet lag";

(VI) 5-methyl cytosine changes in metabolic networks defined in the broadest sense, from the zygote through embryogenesis, foetal development, birth, adolescence, adulthood and old age (including metabolic effects brought about by hypoxia, anoxia, radiation of any type, (be it ionizing or non ionizing, or arising from chemotherapeutic treatments, high altitude exposure radiation from nearby natural sources, such as rocks or from "fallout" from military or government sponsored activities), stress, or by imbalances between the mitochondrial, nuclear or organellar genomes;

(VII) 5-methyl cytosine alterations due to responses at the molecular, cellular, tissue, organ and whole organism levels to proteins, polypeptides, peptides, and DNA, RNA, PNA, INA, ANA, HNA, LNA, CNA, and the like, or peptide aptamers (including any with post translational additions, post translational cleavage products, post translational modifications (such as inteins and exeins, ubiquination and degradation products); proteins, polypeptides and peptides containing rare natural amino acids, as well as single rare amino acids such as D-serine involved in learning, brain growth and cell death; drugs, biopharmaceuticals, chemical entities (where the definitions of Chemical Entities and Biopharmaceuticals is that of G. Ashton, 2001, Nature Biotechnology 19, 307-3111)), metabolites, new salts, prodrugs, esters of existing compounds, vaccines, antigens, polyketides, non-ribosomal peptides, vitamins, and molecules from any natural source (such as the plant derived cyclopamine);

(VIII) 5-methyl cytosine alterations due to responses at the molecular, cellular, tissue, organ and whole organism levels to RNA and DNA viruses be they single or double stranded, from external sources, or internally activated such as in endogenous transposons or retrotransposons, (SINES and LINES);

(IX) 5-methyl cytosine alterations due to responses at the molecular, cellular, tissue, organ and whole organism levels to reverse transcribed copies of RNA transcripts be they of genic or non genic origins, (or intron containing or not);

(X) 5-methyl cytosine alterations due to responses at the molecular, cellular, tissue, organ and whole organism levels to: (a) DNA, RNA, PNA, INA, ANA, HNA, LNA, CNA, and the like (or DNA, RNA, PNA, INA, ANA, HNA, LNA, CNA, aptamers of any in all combinations); including DNA, RNA, PNA, INA, ANA, HNA, LNA, CNA, and the like molecules circulating in all fluids including blood and cerebrospinal fluid as well as maternal fluids before, during and after pregnancy (b) combinations of conjugated biomolecules that are chimeras of peptides and nucleic acids; or chimeras of natural molecules such as cholesterol moieties, hormones and nucleic acids; and (XI) 5-methyl cytosine alterations due to responses of stem cells, (either in vivo, ex vivo or in association with novel environments or natural and synthetic substrates (or combinations thereof), from human and animal origin to any of the perturbations described in (i) to (x) above.

(XII) The analysis may also include conversion of unmethylated nucleic acid to create a genome of essentially 3 bases and then use the regions of created homology to simultaneously detect multiple organisms or variants at once.

Any suitable method for obtaining nucleic acid material can be used. Examples include, but are not limited to, commercially available DNA/RNA kits or reagents, workstation, standard cell lysis buffers containing protease reagents and organic extraction procedures, which are well known to those of skill in the art.

The method can be carried out in a reaction vessel. The reaction vessel can be any suitable vessel such as tube, plate, capillary tube, well, centrifuge tube, microfuge tube, slide, coverslip or any suitable surface. The method is generally carried out in one reaction vessel in order to reduce the likelihood of degradation or loss of the nucleic acid sample.

Generally, the denaturing environment is provided to the sample by adding either an alkali such as NaOH or by heating the nucleic acid containing sample. The alkali environment is provided to denature double stranded DNA acid molecules into a state where the molecules are readily reactive with the bisulphite reagent. It will be appreciated, however, that any other denaturation method such as heat treatment or other suitable alkali or denaturing agent can be added or used such as KOH and any other alkali so long as use of the reagents for denaturation do not significantly inhibit subsequent steps. This can be important for RNA analysis as alkali results in degradation of the RNA molecules therefore another method such as heat denaturation is therefore desirable.

Generally, the bisulphite reagent is sodium metabisulphite. The bisulphite reagent is used to cause sulphonation of cytosine bases to cytosine sulphonate followed by hydrolytic deamination of the cytosine sulphonate to uracil sulphonate. It will be appreciated, however, that any other suitable bisulphite reagent could be used such as sulphite or acetate ions (see Shapiro, R., DiFate, V., and Welcher, M, (1974) J. Am. Chem. Soc. 96: 906-912).

The incubation with the sulphonating reagent can be carried out at pH below 7 and at a temperature which favors the formation of the uracil sulphonate group. A pH below about 7 is preferred for carrying out the sulphonation reaction, which converts the cytosine bases to cytosine sulphonate and subsequently to uracil sulphonate. However, the methods of the invention can be performed with the sulphonation reaction above pH 7, if desired.

The sulphonation reaction can be carried out in the presence of an additive capable of enhancing the bisulphite reaction. Examples of suitable additives include, but not limited to, quinol, urea, methoxyamine. Of these reagents, quinol is a reducing agent. Urea and methyoxyamine are agent added to improve the efficiency of the bisulphite reaction. It will be appreciated that other additives or agents can be provided to assist in the bisulphite reaction.

The sulphonation reaction results in methylated cytosines in the nucleic acid sample remaining unchanged while unmethylated cytosines are converted to uracils.

Reaction conditions found to work well are as follows. The denatured DNA, or other nucleic acids, to be treated is made up to a volume of 20 μl. Then 208 μl of a freshly prepared solution of 2 M sodium metabisulphite (BDH AnalaR #10356.4D) pH 5.0 (the pH is adjusted by the addition of 10M sodium hydroxide (BDH AnalaR #10252.4X) along with 12 μl of a 10 mM quinol solution (BDH AnalaR #103122E). The concentration of quinol added can be anything in the range of about 10 to 500 mM as determined experimentally. The solution is then mixed and overlayed with 208 μl of mineral oil (Sigma molecular biology grade M-5904). The sample is then left overnight at a suitable temperature, for example, room temperature or another suitable temperature, to allow time for full bisulphite conversion. It is understood by those skilled in the art that the volumes, concentrations and incubation time and temperature described above are merely exemplary and can be varied so long as the reaction conditions are suitable for sulphonation of the nucleic acids. It is also understood that the order of the steps of methods of the invention can be varied so long as the sulphonation and de-sulphonation steps are sufficiently carried out.

The dilution step is performed so that the salts inhibitory to subsequent reactions are not co-precipitated with the sulphonated nucleic acids. The salt concentration is diluted to less than about 1 M. Generally, the dilution step is carried out using water or buffer to reduce the salt concentration to below about 0.5M. For example, the salt concentration is generally diluted to less than about 1 mM to about 1 M, in particular, less than about 0.5 M, less than about 0.4 M, less than about 0.3 M, less than about 0.2 M, less than about 0.1 M, less than about 50 mM, less than about 20 mM, less than about 10 mM, or even less than about 1 mM, if desired. One skilled in the art can readily determine a suitable dilution that diminishes salt precipitation with the nucleic acids so that subsequent steps can be performed with minimal further clean up or manipulation of the nucleic acid sample. The dilution is generally carried out in water but can be carried out in any suitable buffer, for example Tris/EDTA or other biological buffers so long as the buffer does not precipitate significantly or cause the salt to precipitate significantly with the nucleic acids so as to inhibit subsequent reactions.

Unlike prior art methods, there is no need to completely separate or isolate the treated nucleic acid from the bisulphite reagent. There is no need to employ chromatography separation methods, for example, as presently required by prior art methods. The dilution step according to the present invention assists in minimizing loss of sample.

Generally, precipitation is carried out using a precipitating agent such as an alcohol. An exemplary alcohol for precipitation of nucleic acids can be selected from isopropanol, ethanol or any other suitable alcohol.

The de-sulphonation step can be carried out by adjusting the pH of the precipitated treated nucleic acid up to about 12.5. Exposure to alkaline environments tends to promote strand breaks in apurinic sites in the nucleic acid induced by the previous exposure to an acidic pH. Therefore, the alkaline pH treatment is minimized if strand breaks are to be avoided. This step can be carried out efficiently at around pH 10.5 with a suitable buffer or alkali reagent. Examples of suitable buffers or alkali reagents include buffers having a pH 7.0-12.5. It will be appreciated by persons skilled in the art that suitable buffers or alkali reagents can be selected from the vast range of known buffers and alkali reagents available.

Temperature ranges for the de-sulphonation step are room temperature to about 96° C. and times can vary from 2 minutes to 96 hours or longer depending on the conditions used. One skilled in the art can readily determine a suitable time and temperature for carrying out the de-sulphonation reaction. Temperatures below room temperature can also be used so long as the incubation time is increased to allow sufficient de-sulphonation. Thus, the incubation step can be carried out at about 10° C., about 20° C., about 22° C., about 25° C., about 30° C., about 35° C., about 37° C., about 40° C., about 45° C., about 50° C., about 55° C., about 60° C., about 65° C., about 70° C., about 75° C., about 80° C., about 85° C., about 90° C., about 95° C., and about 96° C., A particularly useful temperature for carrying out the de-sulphonation reaction is about 55° C. These and other incubation and/or reaction steps can be similarly carried out at various temperatures, as described above, so long as a sufficient reaction step is performed.

The present invention provides methods for the efficient characterization of methylated nucleic acids. The methods allow efficient sulphonation and de-sulphonation steps to be carried out on the nucleic acid sample. However, it is understood that neither of the sulphonation or de-sulphonation steps need be carried out to completion, only sufficiently to subsequently characterize methylation of the nucleic acid, as disclosed herein, or to create sufficient molecules that can be detected via PCR or other methods. One skilled in the art can readily determine whether these steps should be carried out to near completion or whether incomplete reactions are sufficient for a desired analysis. For example, when a small number of cells or a small amount of nucleic acid sample are used, it is generally desired that a more complete reaction be performed. When larger quantities of nucleic acid sample are being characterized, a less complete reaction can be carried out while still providing sufficient reaction products for subsequent analysis of the methylation state of the nucleic acid sample.

As disclosed herein, the invention provides methods for conveniently treating nucleic acids. The methods can be used for the analysis of the methylation state of a nucleic acid population as a measure of the state of a cell, tissue or organism, as disclosed herein. The methods of the invention provide several advantages over methods previously used for treating nucleic acids.

Another advantage of the invention is that the desalting step is carried out in a highly efficient manner by diluting the salt concentration and precipitating the nucleic acids. The dilution step reduces the salt concentration below an amount that, when the nucleic acid is precipitated, does not interfere with subsequent steps such as de-sulphonation. The precipitation step is highly efficient and can optionally include carriers that increase the efficiency of nucleic acid precipitation. Thus, the methods of the invention minimize loss and increase recovery of nucleic acid samples. Accordingly, the methods of the invention provide the additional advantage of allowing even smaller amounts of starting material to be used and efficiently characterized with respect to methylation. The invention provides methods that improve upon the method of Clark et al., 1994 Nucleic Acids Res. 22:2990-2997, by substituting the use of a cumbersome and inefficient chromatography separation method with a simple dilution and precipitation method in the step of removing any unwanted reagents or diluents from the nucleic acids.

Further, the use of a buffer solution at slightly alkaline pH can be used to decrease the likelihood that the nucleic acid of interest becomes substantially fragmented. Increasing the pH of the buffered solution to much above pH 12.5 has been demonstrated to lead to very substantial fragmentation of high molecular weight nucleic acids. Therefore, when it is desired to minimize such fragmentation, an alkaline pH below about pH 11 is generally used.

Yet another advantage of the invention is that the reactions can be carried out in a single tube or vessel for each sample, thus minimizing sample loss and allowing the processing of numerous samples. A further advantage of the method of the invention compared to previous methods is that the nucleic acids, once sulphonated, can be resuspended in a buffer having a basic pH to carry out the de-sulphonation step rather than requiring the addition of strong base and the subsequent removal of salts, as in the method described by Clark et al, 1994.

Still another advantage is that the methods of the invention allow the optional digestion with restriction enzymes prior to treatment. The traditional bisulphite treatment method generally includes an initial digestion step with a restriction enzyme for successful treatment and amplification and is therefore not applicable to long distance PCR reactions. However, the methods of the invention do not require pre-digestion with restriction enzymes prior to the sulphonation reaction, again allowing fewer manipulations as well as the option of performing PCR on longer fragments.

The methods of the invention can be used to characterize the methylation state of a cell, tissue or organism. The methods of the invention can also be used in conjunction with genomic sequencing methods such as those described by Frommer et al., Proc. Natl. Acad. Sci. USA 89:1827-1831 (1992), which is incorporated herein by reference.

The invention additionally provides a method of determining the methylation state of a sample. The method can be carried out on a sample using the method of the invention for treatment of nucleic acids, that is, the HGS method. The method for determining the methylation state of a sample can be carried out in parallel with a test sample and a control sample so that the methylation state of the sample can be compared and determined relative to a reference sample. For example, the samples can be compared to determine whether there is an increase or decrease of methylation in general or at particular sites. Such a determination can be used to diagnose and/or determine the prognosis of a disease, as discussed herein. The method can further include reporting of the methylation state of a sample, for example, in a diagnostic application. It may also be used in a methylation independent manner, as in the detection of multiple sequences that have become more similar after conversion with bisulphite.

The methods according to the present invention are particularly suitable for use in kits. Such kits typically contain reagents and instructions to carry out the invention. By providing suitable kits, it is possible to allow end users to carry out work on methylated nucleic acid with reproducible and consistent results.

It is understood that the components of the method of the invention can be provided in the form of a kit. The kit can contain appropriate chemical reagents, reaction tubes and instructions for carrying out the method of the invention.

EXAMPLES

Methods and Reagents

Chemicals were obtained as follows: Agarose from Bio-Rad (Hercules Calif.; certified molecular biology grade #161-3101); Acetic acid, glacial, from BDH (Kylsyth, Australia; AnalaR 100015N); ethylenediamine tetraacetic acid (EDTA) from BDH (AnalaR 10093.5V); Ethanol from Aldrich (St. Louis Mo.; 200 proof E702-3); Isopropanol from Sigma (St. Louis Mo.; 99%+Sigma 1-9516); Mineral oil from Sigma (M-5904); Sodium acetate solution 3M from Sigma (S-7899); Sodium chloride from Sigma (ACS reagent S9888); and Sodium hydroxide from BDH (AnalaR #10252.4X).

Enzymes/Reagents were obtained as follows: EcoR1 from Roche (Indianapolis Ind.; #87930626, 10 units/µl); HindIII from Biolabs (Beverly Mass.; #R01045, 10 units/µl); PCR master mix from Promega (Madison Wis.; #M7505); and DNA markers from Sigma (Direct load PCR low ladder 100-1000 bp, Sigma D-3687 and 100-10 Kb, Sigma D-7058).

Solutions were as follows: (1) 10 mM Tris/0.1M EDTA, pH 7.0-12.5; (2) 3M NaOH (6 g in 50 ml water; BDH AnalaR #10252.4X); (3) 2M Metabisulphite (7.6 g in 20 ml water with 416 µl 10 N NaOH (BDH AnalaR #10356.4D); (4) 10 mM Quinol (0.055 g in 50 ml water; BDH AnalaR #103122E); (5) 50×TAE gel electrophoresis buffer (242 g Trizma base, 57.1 ml glacial acetic acid, 37.2 g EDTA and water to 1l); and (6) 5× Agarose gel loading buffer (1 ml 1% Bromophenol blue (Sigma B6131), 1 ml Xylene Cyanol (Sigma X-4126), 3.2 ml Glycerol (Sigma G6279), 8 µl 0.5M EDTA pH 8.0, 200 µl 50×TAE buffer and water to 10 ml).

Tissues and Cell Lines

Tissues and cell lines were obtained as follows: HeLa (cervical cancer cell line, ATCC CCL-2); LNCaP (prostate cancer cell line, ATCC #CRL-10995); HepG2 (liver cancer cell line, ATCC #HB-8065); and MCF-7 (breast cancer cell line, ATCC #HTB-22) were obtained from American Type Culture Collection.

For preparation of T-medium for growth of LNCaP Cells, reagents were obtained from Gibco/BRL or Invitrogen, except as indicated, as follows: DMEM powder 10× sachets (10×1l; #31600-034); F-12K Nutrient mixture, Kaighn's Modifn. (500 ml; #21127-022); L-Glutamine, 200 mM (100 ml; #25030-081); Penicillin/Streptomycin 5000 U/ml, 5000 µg/ml (100 ml #15070-063 Thermo Trace); Foetal Bovine serum (500 ml; #15-010-0500V Sigma); Insulin (Bovine pancreas) (100 mg; #11882); Transferrin (Human) (10 mg; # T5391); d-Biotin (500 mg; #B4639); Adenine (5 g; # A3159); T3 (#T6397 or #T5516).

T-media (500 ml) was prepared as follows: DMEM stock solution was prepared, by adding 3.7 g Sodium bicarbonate per liter and adjusting the pH to between 7.2-7.4. To 400 ml of DMEM stock solution, the following reagents were added: 100 ml of F-12K; 250 µl of insulin (10 mg/ml); 1.0 ml T3 (500×; Tri-iodothyronine; 6.825 ng/ml); 1.0 ml transferrin (500×; 2.5 mg/ml); 1.0 ml Biotin (500×; 0.122 mg/ml); 4.0 ml Adenine (125×; 3.125 mg/ml); 5.5 ml Penicillin/Streptomycin (100×; 5000 µg/ml); and 5.5 ml Glutamine (100×; 200 mM). After sterile filtration, 50 ml of Foetal Bovine Serum was added to give 10%.

Table 1 sets out the cell lines and growing conditions used in the experiments outlined below.

| Name | Cell Type | Growing Conditions |
| --- | --- | --- |
| BL13 | Bladder Cancer | RPM1 + 10% HI FCS Split 1:3, 2x week |
| DU145 | Prostate Cancer (unmethylated) | RPM1 + 10% HI FCS + 2 mM Glutamine Split 1:6, 2x week |
| HeLa | Cervical Carcinoma | RPM1 + 10% HI FCS for initial rapid growth then DMEM + 10% HI FCS for slower growth. Split 1:10, 2x week |
| HepG2 | Liver Carcinoma | DMEM (high glucose 4.5 g/L) + 10% HI FCS + 2 mM Glutamine. Split 1:4 2x week |
| LNCAP | Prostate Cancer (Methylated) | DMEM (low glucose) + 10% HI FCS + 2 mM Glutamine + Lots of other nutrients, see LNCaP growth method sheet. |
| MCF7 | Breast Cancer | RPM1 + 10% HI FCS Split 1:6, 2x week |

Purification of T-cells and CD34+ Cells from Whole Blood

Samples were obtained from a patient undergoing leukapheresis at the Royal North Shore Hospital, Sydney. Samples were obtained with prior Ethics Committee approval. White blood cells were concentrated using Ficoll Paque plus (Amersham Biosciences #17-1440-03; Piscataway N.J.) according to the manufacturers instructions. T-cells and CD34+ cells were isolated from the white cell population using CELLection CD2 Dynabeads (Dynal #116.03; Lake Success N.Y.) and Dynal CD34 Progenitor Cell selection system (Dynal #113.01) respectively according to the manufactures instructions.

The following equipment was used: the PCR machine was ThermalHybaid PX2 (Sydney, Australia) the Gel Documentation System was a Kodak UVItec EDAS 290 (Rochester N.Y.), and the microfuge was an Eppendorf 5415-D (Brinkman Instruments; Westbury N.Y.).

DNA Amplification

PCR amplifications were performed in 25 µl reaction mixtures containing 2 µl of bisulphite-treated genomic DNA, using the Promega PCR master mix, 6 ng/µl of each of the primers. The strand-specific nested primers used for amplification of GSTP1 from bisulphite-treated DNA are GST-9 (967-993) TTTGTTGTTTGTTTATTTTTTAGGTTT (SEQ ID NO: 1); (F) GST-10 (1307-1332) AACCTAATACTAC-CAATTAACCCCAT (SEQ ID NO:2) (R), GST-11 (999-1027) GGGATTTGGGAAAGAGGGAAAGGTTTTTT (SEQ ID NO:3) (F); GST-12 (1281-1306) ACT-AAAAACTCTAAAAACCCCATCCC (SEQ ID NO:4) (R). The location of the primers is indicted according to the GSTP1 sequence (Accession number: M24485; GenBank citation Morrow et al., Gene 75:3-11 (1989)).

RNA Purification

Du145 cells were grown to 90% confluence in T75 tissue culture flasks under the conditions described above. The media was discarded and 3 ml of Trizol (Invitrogen Cat# 15596-026) added and the samples processed as follows:—

I. Samples were mixed well and left at room temperature for 5 minutes to dissociate nucleoprotein complexes.

II. The samples were then spun at 12,000×g for 10 minutes at 4° C. to remove high molecular weight DNA and other contaminants.

III. The supernatant was removed into a clean tube and 100 µl of 100% chloroform added and the samples were mixed vigorously by hand for 15 seconds then incubated at room temperature for 2-3 minutes.

IV. The samples were then spun at 12,000×g for 10 minutes at 4° C. to separate the phases.

V. The upper aqueous phase was removed into a clean tube ensuring the pipette tip stayed away from the interface and 1 µl of 20 mg/ml glycogen added and the samples vortexed.

VI. An equal volume of 100% (0.25 ml) was added the tubes vortexed then left at room temperature for 10 minutes.

VII. The samples were then spun at 12,000×g for 10 minutes at 4° C. to pellet the RNA.

VIII. The supernatant was removed and the pellet washed with 0.75 ml of 80% ethanol to removed inhibitors of the cDNA synthesis reaction, vortexed briefly, then spun at 7,500×g for 5 minutes at 4° C. to pellet the RNA.

IX. Step VIII was repeated a further time.

X. The pellet was then spun in a microfuge for 10 seconds, the residual ethanol removed and the pellet immediately resuspended in 25 µl of RNase free water. NB if the pellet dries out then it is very difficult to resuspend the RNA and the 260/280 ratio will be less than 1.6.

XI. The OD 260/280/310 is then recorded.

XII. Purified RNA was then stored at −70° C. until required cDNA Synthesis cDNA synthesis was performed using SUPERSCRIPT® Reverse Transcriptase (Invitrogen Cat# 18080-044) with 100 ng random hexamers (Invitrogen Cat# 48910-011) as recommended by the manufacturers instructions.

RNA Amplification

PCR amplifications were performed in 25 µl reaction mixtures containing 2 µl of bisulphite-treated reverse transcribed genomic RNA, using the Promega PCR master mix, 6 ng/µl of each of the primers. The strand-specific primers used for amplification of Actin from bisulphite-treated RNA were ActinBS-3A (2076-2097) TTAATATTTTAGTTATGTATGTTGT SEQ ID NO:5); ActinBS-4 (2720-2744) CTTCATTATACTAAATACCAAA (SEQ ID NO:6).

Control primers against wild type actin RNA were also included to ensure that the RNA amplified originated from bisulphite converted RNA and not that of wild type RNA. The following wild type primers were synthesised Actin wild-type 3A (2076-2097) TCAACACCCCAGCCATGTACGTTGC (SEQ ID NO:7), Actin wild-type 4 (2720-2744) GATCTTCATTGTGCTGGGTGCC (SEQ ID NO:8). The location of the primers is indicted according to the human beta-actin gene sequence (Accession number: M10277).

Nucleic Acid Separation

1% or 2% agarose gels were prepared in 1% TAE containing 1 drop ethidium bromide (CLP #5450) per 50 ml of agarose. The DNA or RNA sample of interest (genomic or PCR derived) was mixed with $1/5^{th}$ volume 5× agarose loading buffer and electrophoresed at 125 mA in X1 TAE using a submarine horizontal electrophoresis tank.

Removal of Bisulphite and Other Unwanted Reagents

Following treatment of the nucleic acid sample, bisulphite and any other unwanted reagent can be removed prior to de-sulphonation by any separation technique. Examples include, but not limited to, precipitation, binding and elution from solid supports. Examples of solid supports include glass, silica and ion exchange media. Silica include magnetite beads: Kisker beads (modified and unmodified), MagSi (MagnaMedics) and Progentech beads, beads with switchable surface charge include CHARGESWITCH® beads (Invitrogen), and Glass-beads include Roche MAGNA PURE® beads.

Traditional Bisulphite Treatment of DNA (Clark et al., (1994) Nucleic Acids Res. 22:2990-2997, which is incorporated herein by reference) (prior art method that results extremely in poor yields of DNA)

Genomic DNA (2 µg) was digested with Eco R1 for 60 minutes at least in a final volume of 20 µl. To this digest, 2.2 µl of 3M NaOH (6 g NaOH/50 ml water, made fresh) were added and incubated at 37° C. for 15 minutes. A 208 µl volume of 2M Metabisulphite (7.6 g metabisulphite/20 ml water and 416 µl 10M NaOH to pH 5.0) was added followed by 12 µl of 10 mM quinone (0.55 g hydroquinone gives 100 mM, dilute $1/10$). The reaction mixture was overlaid with 200 µl of mineral oil and incubated at 50-55° C. overnight. At the end of the incubation, the mineral oil was removed and 1 µg yeast tRNA (Sigma R-8508) was added.

DNA desalting was carried out using the Wizard DNA clean up system (Promega #A7280) according to the manufactures instructions. Briefly, 1 ml of resin was added to the sample and the sample vortexed. The sample was applied to a column attached to a 2.5 ml syringe and pushed through the syringe gently. The column was washed with 2 ml of 80% isopropanol and then spun for 20 seconds at 14,000 rpm in a microfuge. Fifty µl of water was applied to the column and the sample left for 1 minute at room temperature. The column material was applied to a clean 1.5 ml centrifuge tube and was spun for 20 seconds at 14,000 rpm in a microfuge. The DNA was recovered in the eluted volume, ready for de-sulphonation.

To remove the sulphate groups from uracil, 5.5 µl of 3M NaOH were added to the eluted DNA and the mixture was incubated at 37° C. for 15 minutes. A 33.5 µl volume of $NH_4OAC$ (pH 7.0) was added to neutralize the alkali. A 330 µl of 100% ethanol was added, and the reaction mixture was incubated at −20° C. for 60 minutes. The sample was spun 15 minutes at 14,000 rpm and the ethanol was discarded. The pellet was air dried and resuspended in 10 µl T/E (pH 8.0).

HGS Bisulphite Treatment of Nucleic Acid

An exemplary protocol demonstrating the effectiveness of the bisulphite treatment according to the present invention is set out below. The protocol successfully resulted in retaining substantially all nucleic acid treated. This method of the invention is also referred to herein as the HGS bisulphite method. It will be appreciated that the volumes or amounts of sample or reagents can be varied.

DNA Denaturation

To 2 µg of DNA, which can be pre-digested with suitable restriction enzymes if so desired, 2 µl ($1/10$ volume) of 3 M NaOH (6 g in 50 ml water, freshly made) was added in a final volume of 20 µl. This step denatures the double stranded DNA molecules into a single stranded form, since the bisulphite reagent preferably reacts with single stranded molecules. The mixture was incubated at 37° C. for 15 minutes. Incubation at temperatures above room temperature can be used to improve the efficiency of denaturation RNA Denaturation Two µg of RNA was resuspended in a total volume of 20 µl containing 1 µl of RNase inhibitor (RNaseOUT Invitrogen Cat# 10777-019 40 U/µl). This solution was then heated at 50° C. for 2 minutes then snap chilled on ice (optional). This step denatures the RNA molecules into a form essentially free of secondary structure, as the bisulphite reagent preferably reacts with single stranded molecules.

Bisulphite Treatment of DNA

After the incubation, 208 µl 2 M Sodium Metabisulphite (7.6 g in 20 ml water with 416 ml 10 N NaOH; BDH AnalaR #10356.4D; freshly made) and 12 µl of 10 mM Quinol (0.055 g in 50 ml water, BDH AnalR #103122E; freshly made) were added in succession. Quinol is a reducing agent and helps to reduce oxidation of the reagents. Other reducing agents can also be used, for example, dithiothreitol (DTT), mercaptoethanol, quinone (hydroquinone), or other suitable reducing agents. The sample was overlaid with 200 µl of mineral oil. The overlaying of mineral oil prevents evaporation and oxidation of the reagents but is not essential. The sample was then incubated overnight at 55° C. Alternatively the samples can be cycled in a thermal cycler as follows: incubate for about 4 hours or overnight as follows: Step 1, 55° C./2 hr cycled in PCR machine; Step 2, 95° C./2 min. Step 1 can be performed at any temperature from about 37° C. to about 90° C. and can vary in length from 5 minutes to 8 hours. Step 2 can be performed at any temperature from about 70° C. to about 99° C. and can vary in length from about 1 second to 60 minutes, or longer.

After the treatment with Sodium Metabisulphite, the oil was removed, and 1 µl tRNA (20 mg/ml) or 2 µl glycogen were added if the DNA concentration was low. These additives are optional and can be used to improve the yield of DNA obtained by co-precipitating with the target DNA especially when the DNA is present at low concentrations. The use of additives as carrier for more efficient precipitation of nucleic acids is generally desired when the amount nucleic acid is <0.5 µg.

An isopropanol cleanup treatment was performed as follows: 800 μl of water were added to the sample, mixed and then 1 ml isopropanol was added. The water or buffer reduces the concentration of the bisulphite salt in the reaction vessel to a level at which the salt will not precipitate along with the target nucleic acid of interest. The dilution is generally about ¼ to ¹⁄₁₀₀₀ so long as the salt concentration is diluted below a desired range, as disclosed herein.

The sample was mixed again and left at 4° C. for a minimum of 5 minutes. The sample was spun in a microfuge for 10-15 minutes and the pellet was washed 2× with 80% ETOH, vortexing each time. This washing treatment removes any residual salts that precipitated with the nucleic acids.

The pellet was allowed to dry and then resuspended in a suitable volume of T/E (10 mM Tris/0.1 mM EDTA) pH 7.0-12.5 such as 50 μl. Buffer at pH 10.5 has been found to be particularly effective. The sample was incubated at 37° C. to 95° C. for 1 min to 96 hr, as needed to suspend the nucleic acids.

The method described above can be preceded by digestion with one or more restriction enzymes. Two independent restriction enzyme digests are set up of the same sample of DNA as described below. The enzymes selected for digestion are dependent upon the sequence to be amplified. For example, digest 2 μg genomic DNA with EcoRI in a 20 μl volume for 1 hr/at 37° C. This step is used to digest the genomic DNA into smaller fragments which are more amenable to bisulphite conversion than genomic DNA. Sonication or physical forces can also be used to shear the DNA into smaller sized fragments. The intensity of sonication and the length of sonication is selected based on the desired size of DNA fragments. A separate digestion reaction is carried out, for example, by digesting 2 μg genomic DNA with HindIII as described above. These or other suitable restriction enzymes can be selected for pretreatment digestion. The digested DNA is treated with metabisulfite as described above.

Bisulphite Treatment of RNA

After the incubation, 208 μl 2 M Sodium Metabisulphite (7.6 g in 20 ml water with 416 ml 10 N NaOH; BDH AnalaR #10356.4D; freshly made) was added. The sample was overlaid with 200 μl of mineral oil. The overlaying of mineral oil prevents evaporation and oxidation of the reagents but is not essential. The sample was then incubated 3 hours to overnight at 37° C. to 55° C. Alternatively the samples can be cycled in a thermal cycler as follows: incubate for about 4 hours or overnight as follows: Step 1, 55° C./2 hr cycled in PCR machine; Step 2, 70° C./30 seconds. Step 1 can be performed at any temperature from about 37° C. to about 90° C. and can vary in length from 5 minutes to 8 hours. Step 2 can be performed at any temperature from about 60° C. to about 99° C. and can vary in length from about 1 second to 60 minutes, or longer.

After the treatment with Sodium Metabisulphite, the oil was removed, and 1 μl glycogen was added if the RNA concentration was low. This additive is optional and can be used to improve the yield of RNA obtained by co-precipitating with the target RNA especially when the RNA is present at low concentrations. The use of additives as carrier for more efficient precipitation of nucleic acids is generally desired when the amount nucleic acid is <0.5 μg.

An isopropanol cleanup treatment was performed as follows: 800 μl of water were added to the sample, mixed and then 1 ml isopropanol was added. The water or buffer reduces the concentration of the bisulphite salt in the reaction vessel to a level at which the salt will not precipitate along with the target nucleic acid of interest. The dilution is generally about ¼ to ¹⁄₁₀₀₀ so long as the salt concentration is diluted below a desired range, as disclosed herein.

The sample was mixed again and left at room temperature for 15 minutes. The sample was spun in a microfuge for 10-15 minutes and the pellet was washed 2× with 80% ETOH, vortexing between washes. This washing treatment removes any residual salts that precipitated with the nucleic acids.

The pellet was allowed to dry and then resuspended in a suitable volume of T/E (10 mM Tris/0.1 mM EDTA) pH 7.0-12.5 such as 50 ul. Buffer at pH 10.5 has been found to be particularly effective. The sample was incubated at 37° C. to 95° C. for 1 min to 96 hr, as needed to suspend the nucleic acids.

Sonication or physical forces can also be used to shear the RNA into smaller sized fragments. The intensity of sonication and the length of sonication is selected based on the desired size of RNA fragments.

Results

DNA Analysis of LNCaP Cells and Sensitivity of PCR Amplification

Cultures of LNCaP cells were grown under standard conditions to 90% confluence. Cells were trypsinised, washed, then counted using a haemocytometer. Cells were then diluted to contain the approximate number of cells as indicated in Table 2. The cells were then lysed using MASTERPURE™ DNA Purification kit (Epicentre #MCD85201; Madison Wis.) as described by the manufacturers instructions and the DNA then modified using the two sulphonation methods described above.

After accurate determination of cell numbers, cultures were split in duplicate into 1.5 ml eppendorf centrifuge tubes at the following cell numbers 100, 1000, 10000 and 100000 in 25 μl of T/E pH 8.0. Cell lysis was then performed on the cells as described by the manufacture's instructions MASTERPURE™ DNA Purification kit (Epicentre #MCD85201) as described by the manufacturers instructions.

DNA was resuspended in 10 μl of T/E pH 8.0. DNA was then digested with 1 unit of EcoR1 (Roche #87930626 10 units/μl) according to the manufacturers instructions for 1 hour at 37° C. in a final volume of 20 μl.

Traditional bisulphite treatment of DNA (Clark et al 1994) was performed on one set of duplicates while the HGS bisulphite treatment of DNA was performed on the other set. After treatment DNA was resuspended in 5 μl of T/E pH 8.0.

PCR amplification was performed on 1 μl of treated DNA, ⅕$^{th}$ volume of final resuspended sample volume, as follows. PCR amplifications were performed in 25 μl reaction mixtures containing 1 μl of bisulphite-treated genomic DNA, using the Promega PCR master mix, 6 ng/μl of each of the primers. The strand-specific nested primers used for amplification of GSTP1 from bisulphite-treated DNA are GST-9 (967-993) TTTGTTGTTTGTTTATTTTTTAGGTTT (SEQ ID NO:1) (F) GST-10 (1307-1332) AACCTAATACTAC-CAATTAACCCCAT (SEQ ID NO:2) 1$^{st}$ round amplification conditions.

One μl of 1$^{st}$ round amplification was transferred to the second round amplification reaction mixtures containing primers(R) GST-11 (999-1027) GGGATTTGGGAAA-GAGGGAAAGGTTTTTT (SEQ ID NO:3) (F) GST-12 (1281-1306) ACTAAAAACTCTAAAAACCCCATCCC (SEQ ID NO:4) (R). The location of the primers is indicted according to the GSTP1 sequence (Accession number: M24485). Samples of PCR products were amplified in a ThermoHybaid PX2 thermal cycler under the conditions described in Clark et al.

Agarose gels (2%) were prepared in 1% TAE containing 1 drop ethidium bromide (CLP #5450) per 50 ml of agarose.

Five μl of the PCR derived product was mixed with 1 μl of 5× agarose loading buffer and electrophoresed at 125 mA in X1 TAE using a submarine horizontal electrophoresis tank. Markers were the low 100-1000 bp type. Gels were visualised under UV irradiation using the Kodak UVIdoc EDAS 290 system.

Table 2 shows a comparison of the sensitivity of PCR amplification between the HGS method of the invention and the traditional method of Clark et al.

TABLE 2

Sensitivity of PCR-based amplification of the GSTP1 Gene using the HGS method versus traditional bisulphite amplification procedures (Clark et al, 1994)

| | Sensitivity of PCR Amplification | | | |
|---|---|---|---|---|
| Method | 20,000 | 2,000 | 200 | 20 |
| HGS | Yes | Yes | Yes | Yes |
| traditional | Yes | Yes | No | No |

Effect of pH on Degradation of Bisulphite Treated Genomic DNA

Two μg of LNCaP DNA was digested with 2 units of EcoR1 (Roche #87930626 10 units/μl) according to the manufacturers instructions for 1 hour at 37° C. in a final volume of 20 μl. Eight individual reactions were prepared.

HGS bisulphite treatment of DNA was performed on each of the digests. After treatment, DNA from each individual treatment was resuspended in 20 μl of T/E at either pH 7.0, 8.0, 8.5, 9.0, 9.5, 10.0, 10.5 and 12.5.

The DNA was then incubated using the following methods.
Treatment 1. HGS bisulphite treated genomic DNA was resuspended in buffer solution pH 10.5 and left at 37° C. for 30 minutes then PCR amplified.
Treatment 2. HGS bisulphite treated genomic DNA was resuspended in buffer solution pH 10.5 and left at 37° C. for 120 minutes then PCR amplified.
Treatment 3. HGS bisulphite treated genomic DNA was resuspended in buffer solution pH 10.5 and left at 55° C. for 30 minutes then PCR amplified.

A 1% agarose gel was prepared in 1% TAE containing 1 drop ethidium bromide (CLP #5450) per 50 ml of agarose. Ten μl of the genomic DNA sample was mixed with $\frac{1}{5}^{th}$ volume 5× agarose loading buffer (2 μl) and electrophoresed at 125 mA in X1 TAE using a submarine horizontal electrophoresis tank. Markers were the 100-10,000 range. The gel was visualised and photographed under UV irradiation using the Kodak UVIdoc EDAS 290 system.

PCR Analysis on the Samples

PCR amplification was performed on 1 μl of bisulphite treated DNA resuspended sample DNA as follows.

PCR amplifications were performed in 25 μl reaction mixtures containing 1 μl of bisulphite-treated genomic DNA, using the Promega PCR master mix, 6 ng/μl of each of the primers. The strand-specific nested primers used for amplification of GSTP1 from bisulphite-treated DNA are GST-9 (967-993) TTTGTTGTTTGTTTATTTTTTAGGTTT (F) (SEQ ID NO: 1) and GST-10 (1307-1332) AACCTAATAC-TACCAATTAACCCCAT (SEQ ID NO: 2) ($1^{st}$ round amplification conditions).

One μl of $1^{st}$ round amplification was transferred to the second round amplification reaction mixtures containing primers (R) GST-11 (999-1027) GGGATTTGGGAAA-GAGGGAAAGGTTTTTT (SEQ ID NO:3); (F) GST-12 (1281-1306) ACTAAAAACTCTAAAAACCCCATCCC (R) (SEQ ID NO:4). The location of the primers is indicted according to the GSTP1 sequence (Accession number: M24485). Samples PCR products were amplified in a ThermoHybaid PX2 thermal cycler under the conditions described in Clark et al 1994.

Agarose gels (2%) were prepared in 1% TAE containing 1 drop ethidium bromide (CLP #5450) per 50 ml of agarose. Five μl of the PCR derived product was mixed with 1 μl of 5× agarose loading buffer and electrophoresed at 125 mA in X1 TAE using a submarine horizontal electrophoresis tank. Markers were the low 100-1000 bp type. Gels were visualised under UV irradiation using the Kodak UVIdoc EDAS 290 system.

The results are summarized in Table 3. The first point of the results of Table 3 is to demonstrate that when the pH of the bisulphite treated genomic DNA solution is low, then no significant amplification can be detected by standard PCR methods. This is probably due to incomplete de-sulphonation of the bisulphite treated genomic DNA.

The results in Table 3 demonstrate that there is dynamic equilibrium between pH and temperature with regard to the rate of de-sulphonation of the bisulphite treated genomic DNA. If the bisulphite treated genomic DNA is left in low pH solutions, then the rate of de-sulphonation is very slow but can be improved by increasing the temperature of the solution. For example, it may be possible to have the bisulphite treated genomic DNA at pH 7.0, heat it at 72° C., leave it for 48 hours, and then achieve complete de-sulphonation. Likewise, at pH 10.5 the reaction may be finished in 5 minutes at 72° C. Thus, a range of temperatures from room temperature to about 95° C. would be suitable for the present invention. pH ranges from 7.0 to 12.5 and incubation times from about 1 minute to about 96 hours would be suitable. It will be appreciated that various possible combinations of pH, time and temperature would be suitable.

In addition, if the samples were treated with the conventional method, then there would be a large loss of DNA when the bisulphite treated genomic DNA is passed down a size exclusion chromatography column to desalt the solution. It is very likely that at least 50% of the bisulphite treated genomic DNA, if not more, is lost because the conventional columns that are used in the prior art are not designed for single stranded DNA material and there is a large loss. Using the HGS procedure without column purification, the loss by the HGS procedure is miniscule.

TABLE 3

Effect of pH on the degradation of bisulphite treated genomic DNA using the HGS methodology

| | pH of the buffered DNA solution | | | | | | | |
|---|---|---|---|---|---|---|---|---|
| | 7.0 | 8.0 | 8.5 | 9.0 | 9.5 | 10.0 | 10.5 | 12.5 |
| High molecular weight DNA Degraded PCR Product Generation | No | No | No | No | No | No | No | Yes |
| PCR product Treatment 1 | No | No | No | No | No | No | No | Yes |
| PCR product Treatment 2 | ND | ND | ND | ND | ND | Faint | Yes | ND |
| PCR product Treatment 3 | ND | ND | ND | ND | ND | ND | Yes | ND |

Treatment 1. HGS bisulphite treated genomic DNA was resuspended in buffer solution pH 10.5 and left at 37° C. for 30 minutes then PCR amplified.
Treatment 2. HGS bisulphite treated genomic DNA was resuspended in buffer solution pH 10.5 and left at 37° C. for 120 minutes then PCR amplified.
Treatment 3. HGS bisulphite treated genomic DNA was resuspended in buffer solution pH 10.5 and left at 55° C. for 30 minutes then PCR amplified.

Bisulphite Treatment of Various Cell Lines and Tissues

One μg of DNA from the following cell lines and tissue samples were digested with 2 units of EcoR1 (Roche

87930626 10 units/μl) in duplicate according to the manufacturers instructions for 1 hour at 37° C. in a final volume of 20 μl: LNCaP Prostate cancer cell line DNA, MCF-7 Breast cancer cell line DNA, BL-13 Bladder cancer cell line DNA, HepG2 Liver cancer cell line DNA, HeLa cervical cancer cell line DNA, T-cells from purified Patient # 1, and CD34+ cells purified from Patient # 1

HGS bisulphite treatment of DNA was performed on one set of the digests. After treatment, DNA from each individual sample was resuspended in 20 μl of T/E at either pH 10.5 and incubated at 55° C. for 2 hours. Traditional bisulphite treatment of DNA (Clark et al 1994) was performed on the other set in which after the DNA was modified it was resuspended in 20 μl of T/E pH 8.0.

PCR Analysis on the Samples

PCR amplification was performed on 1 μl of both the traditional and HGS bisulphite treated DNA. Six individual genomic loci were analysed for each sample to determine the genomic coverage represented by the HGS and the traditional bisulphite modification methods.

PCR amplifications were performed in 25 μl reaction mixtures containing 1 μl of bisulphite-treated genomic DNA, using the Promega PCR master mix and 6 ng/μl of each of the $1^{st}$ round gene specific primers. One μl of $1^{st}$ round amplification was transferred to the second round gene amplification reaction mixtures containing $2^{nd}$ round gene specific primers. PCR products were amplified in a ThermoHybaid PX2 thermal cycler under the conditions described in Clark et al 1994.

Two % agarose gels were prepared in 1% TAE containing 1 drop ethidium bromide (CLP #5450) per 50 ml of agarose. A 5 μl aliquot of the PCR derived product was mixed with 1 μl of 5× agarose loading buffer and electrophoresed at 125 mA in X1 TAE using a submarine horizontal electrophoresis tank. Markers were the low 100-1000 bp type. Gels were visualised under UV irradiation using the Kodak UVIdoc EDAS 290 system.

Genomic DNA treated with the HGS bisulphite method was amplified using conventional PCR technologies with primers designed to detect the GSTP1 gene. The results of the comparison between the prior art method and the method according to the present invention are set out in Table 4.

TABLE 4

Whole Genome Amplification efficiency of HGS method versus traditional bisulphite amplification Procedures (Clark et al, 1994)

| Tissue | HGS method amplification of Gene 1-6 | | | | | | Traditional Bisulphite amplification of Gene 1-6 | | | | | |
|---|---|---|---|---|---|---|---|---|---|---|---|---|
| | 1 | 2 | 3 | 4 | 5 | 6 | 1 | 2 | 3 | 4 | 5 | 6 |
| a | yes | yes | yes | yes | yes | yes | no | no | no | no | no | no |
| b | yes | yes | yes | yes | yes | yes | no | yes | yes | no | no | no |
| c | yes | yes | yes | yes | yes | yes | yes | yes | yes | yes | no | yes |
| d | yes | yes | yes | yes | yes | yes | no | yes | yes | no | no | no |
| e | yes | yes | yes | yes | yes | yes | yes | yes | no | no | yes | yes |
| f | yes | yes | yes | yes | yes | yes | yes | yes | no | no | no | no |

Tissue samples of Table 4 are as follows:
a) LNCaP Prostate cancer cell line DNA
b) MCF-7 Breast cancer cell line DNA
c) HepG2 Liver cancer cell line DNA
d) HeLa cervical cancer cell line DNA
e) T-cells from purified Patient # 1
f) CD34+ cells purified from Patient # 1

FIG. 1 shows comparison of recovery of bisulphite-treated DNA from various tissue samples between the HGS bisulphite method and traditional bisulphite method (Clark et al 1994). Well #1. DNA extracted from 2 LNCaP cells and treated with bisulphite, Well #2. DNA extracted from 20 LNCaP cells and treated with bisulphite, Well #3. DNA extracted from 200 LNCaP cells and treated with bisulphite, Well #4. DNA extracted from 2,000 LNCaP cells and treated with bisulphite and Well #5. DNA extracted from 20,000 LNCaP cells and treated with bisulphite. As can be seen from FIG. 1, the recovery of DNA using the method according to the present invention is vastly superior to that of the prior art method.

RNA Results

Figure 2:
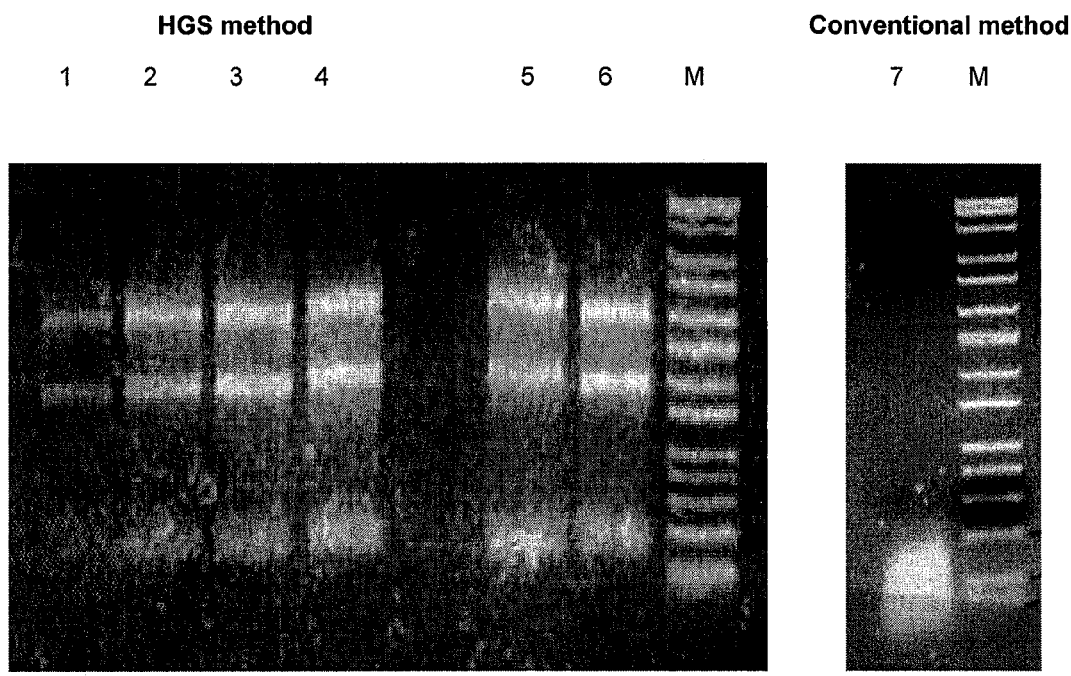
FIG. 2 shows results obtained using the HGS bisulphite treatment on RNA extracted from the prostate cancer cell line Du145 compared to using the conventional bisulphite approach. Lane 1 untreated control RNA, Lane 2 bisulphite treated RNA at 4° C. overnight, Lane 3 bisulphite treated RNA at room temperature overnight, Lane 4 bisulphite treated RNA at 55° C. overnight. Lane 5 bisulphite treated RNA at room temperature overnight replicate #2, lane 6 bisulphite treated RNA at room temperature overnight replicate #3. Lane 7 bisulphite treated RNA at room temperature overnight using the conventional method (Clark et al 1994). M=molecular size markers.

FIG. 2 shows results obtained using the HGS bisulphite treatment on RNA extracted from the prostate cancer cell line Du145 compared to using the conventional bisulphite approach.

As can be seen, high molecular weight RNA was observed in all samples treated with the HGS method at 4° C., room temperature and 55° C. The 23S, 18S and 5S ribosomal RNA bands are clearly visible and it can also be seen that there is very little degradation of the RNA when compared to the control. In contrast, RNA treated by the conventional method has been totally degraded.

Figure 3:
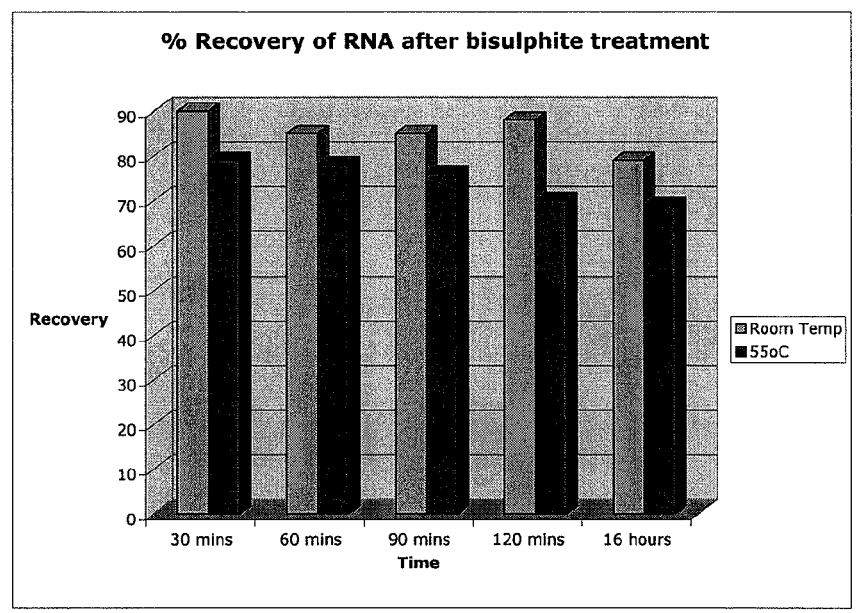
FIG. 3 shows a time course experiment on the stability of the RNA using different temperature incubations. From the result it can be seen that a small amount of degradation takes place in the $1^{st}$ 30 minutes of incubation but then reaches an almost steady state and very little is lost subsequently even after 16 hour incubation at 55° C.

FIG. 3 shows a time course experiment on the stability of the RNA using different temperature incubations. From the result it can be seen that a small amount of degradation takes place in the $1^{st}$ 30 minutes of incubation but then reaches an almost steady state and very little is lost subsequently even after 16 hour incubation at 55° C.

Figure 4:
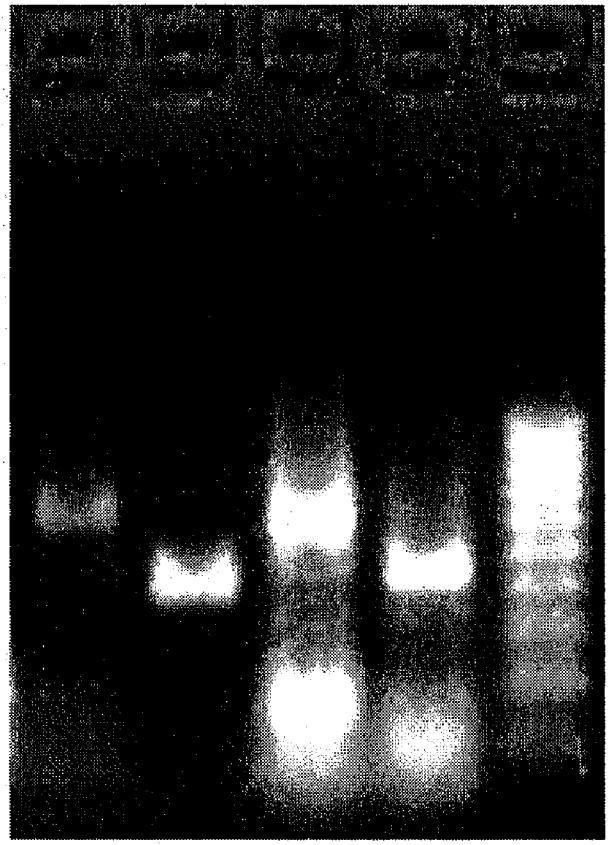
FIG. 4 shows Reverse Transcriptase PCR performed on both bisulphite converted RNA and wild type RNA. As can be seen strong PCR amplification signals are seen in the bisulphite treated RNA at the same size as the bands in the wild type RNA. Lane 1. RT-PCR amplification using bisulphite primers to amplify exon 3 and 4 of bisulphite treated human beta-actin RNA. Lane 2. RT-PCR amplification using bisulphite primers to amplify exon 3 of bisulphite treated human beta-actin RNA. Lane 3. RT-PCR amplification using wild type primers to amplify exon 3 and 4 of human beta-actin RNA. Lane 4. RT-PCR amplification using wild primers to amplify exon 3 of human beta-actin RNA. M=size markers. NB; no PCR amplification was observed when bisulphite treated amplification primers were used on wild type RNA, and additionally no PCR signals were observed when wild type primers were used on bisulphite treated RNA.

FIG. 4 shows Reverse Transcriptase PCR performed on both bisulphite converted RNA and wild type RNA. As can be seen strong PCR amplification signals are seen in the bisulphite treated RNA at the same size as the bands in the wild type RNA.

When bisulphite treated RNA was used as a template for RT-PCR using wild type primers or when wild type RNA was used as a template for RT-PCR with bisulphite converted primers no bands were detected. This indicates that the bisulphite reaction has converted with near 100% efficiency the wild type RNA into converted RNA.

FIG. 5 shows confirmation that the PCR products generated in FIG. 4 were derived from the bisulphite treated genomic RNA. The arrow shows the splice site between exon 3 and 4 in the human beta-actin transcript.

Effects of pH and Temperature on De-Sulfonation Step

To demonstrate the improvement of the invention over other methods, experiments were carried out to determine the effects of pH and temperature on the de-sulfonation step used in the bisulphite treatment of DNA. Experiments were designed to determine the amount of DNA degradation when converting cytosine residues to uracil in DNA using sodium bisulphite in various conditions. The results of the experiments demonstrated the unexpected results obtained when the method is carried out using a de-sulfonation pH of between 10 and less than 12.5 at temperatures between 70° C. and 95° C. compared to the prior art de-sulfonation pH of 9 or 13 at temperatures around 37° C.

To test the affect of pH and temperature on the de-sulfonation step, the following experiments were carried out and a summary of the data obtained is provided below.

Methods

6 μg of Promega human genomic DNA was converted using sodium bisulphite solution as provided in the METHYLEASY™ commercial kit in 8 independent reactions each containing 2 μg of DNA. The reactions were carried out at 55° C. for 7.5 hours. All of the samples were pooled post incubation and mixed well and then re-aliquotted into 8 equal amounts into eight 2 ml Eppendorf tubes. 20 μg of glycogen (Roche) and 800 μl of METHYLEASY™ reagent 4 was added to each tube, mixed well and added 1 ml of isopropanol to each tube and incubated at 4° C. overnight.

All samples were then centrifuged at 4° C. for 20 min, washed with 70% ethanol and resuspended in 200 μL of pH adjusted reagent 3, with the following pH values:
1) 8.06,
2) 9.03
3) 10.02
4) 10.99
5) 12.02
6) 12.49
7) 13.00

Ten μl of each sample was desulphonated for 20 min at 65° C., 70° C., 80° C., 85° C., and 95° C. and then 2 μl was added to the 1$^{st}$ round of a PCR amplification for the hmGST gene, as provided in the MethylEasy™ kit.
2× Promega mastermix=12.5 μl
Outer Primer 1=1.0 μl
Outer Primer 2=1.01
Bisulphite converted DNA=2.0 μl
Nuclease Free Water=8.5 μl
Total=25.0 μl
PCR conditions: (95° C.×3')×1; (95° C.×1', 50° C.×2', 72° C.×2')×30; (72° C.×5')×1
1.5 μl of the above was added to the following pre-mix:
2× Promega mastermix=12.5 μl
Inner Primer 1=1.0 μl
Inner Primer 2=1.0 μl
Syto-9 intercalating dye=1.0 μl
Nuclease Free Water=8.0 μl
Total=23.5 μl The above PCR was run on a Corbett Rotor-Gene™ 6000 instrument using the following profile:

(95° C.×1')×1; (95° C.×5", 50° C.×1.5°, 72° C.×1.5°, 75° C.×1")×30

Figure 6:
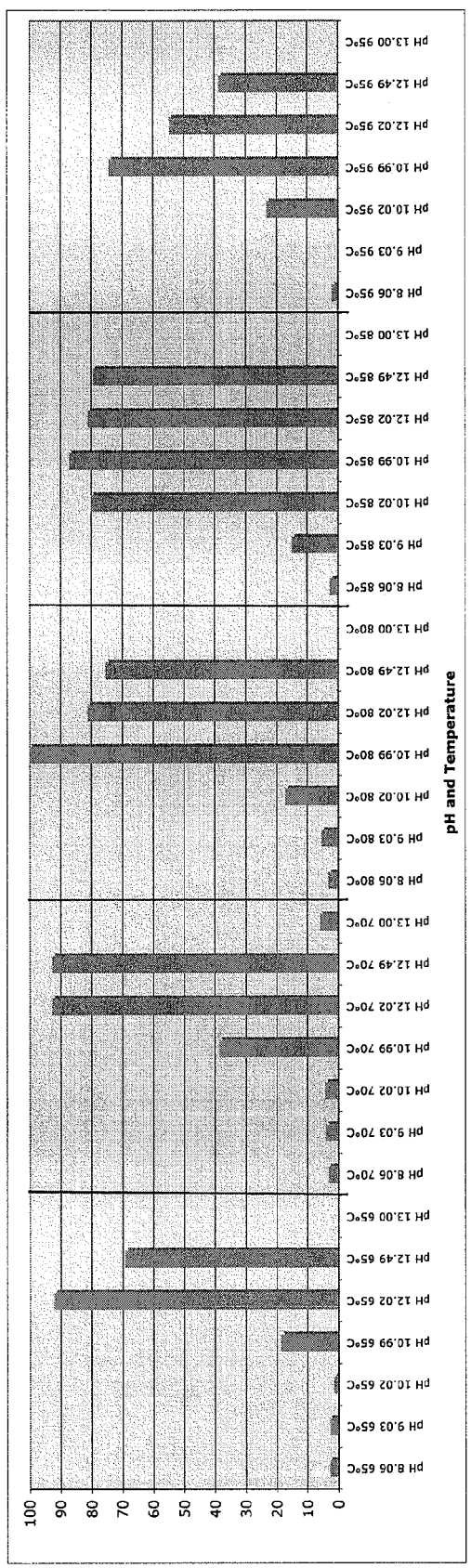
FIG. 6 shows results of the affect of pH and temperature on the de-sulphonation step by relative expression using a standard delta Ct analysis. Experiments were designed to determine the amount of DNA degradation when converting cytosine residues to uracil in DNA using sodium bisulphite in various conditions.

Data was collected and analysed at the 75° C. time point to be free of any primer dimer fluorescence. Using a standard delta Ct analysis, relative expression was determined and was plotted and the results set out in (FIG. 6).

The data shows that de-sulphonation at pH 13, under all temperatures tested, no DNA amplification was detected. This clearly demonstrates that the typical de-sulphonation pH used in the prior art does not work in accordance with the present invention.

From the results obtained, it was found that de-sulphonation using a pH range of 10 to approximately 12.5 at temperature at 65° C. was not as good at preserving the original DNA compared with de-sulphonation using temperatures between 70° C. and 95° C. at the same pH range. Temperatures higher than 95° C. can result in unwanted destruction of DNA so are not generally used when handling DNA.

From the results obtained, de-sulphonation using a pH range of 10 to approximately 12.5 was far better at preserving the original DNA than de-sulphonation using a higher or lower pH.

To determine whether there may have been a "buffer effect" in the de-sulphonation reaction, experiments were carried out at the same pH using either NaOH in a buffer (TE) or using NaOH in water. DNA yields between the same pH were compared.

Figure 7:
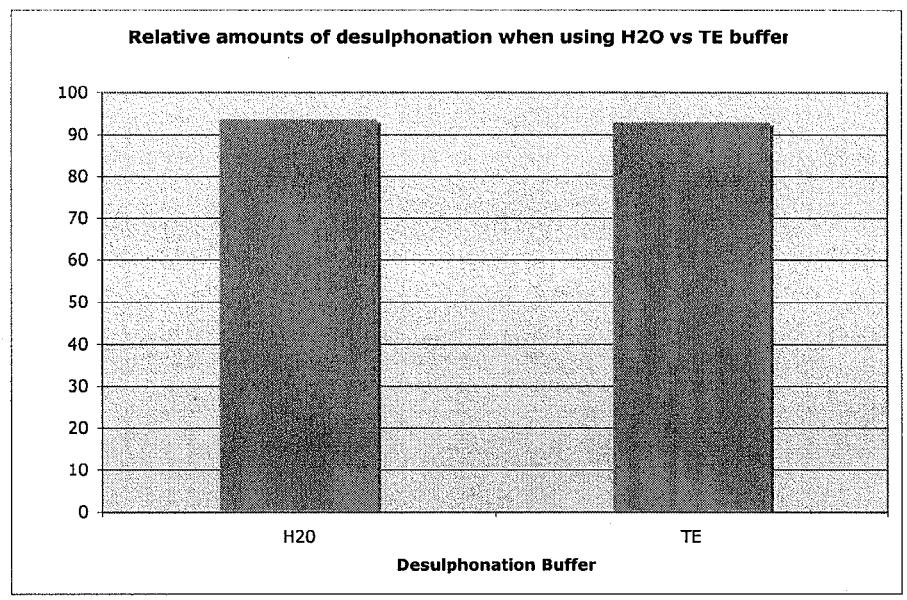
FIG. 7 shows results of comparison between buffer and water on the de-sulphonation reaction.

2×33.3 ng of DNA (Promega human DNA) was converted with sodium bisulphite using standard METHYLEASY™ conditions for 4 hours at 80° C. The converted DNA was desalted and resuspended in either water or in buffer that had been pH adjusted to 10.0 for de-sulphonation reaction. It can be clearly seen from the results in FIG. 7 that buffer had no effect on the de-sulphonation reaction. Only a pH range of 10 to approximately 12.5 is required to be carried out, irrespective of the diluent used.

Detecting methylation in DNA in the accordance with the present invention out performs prior art methods. The present invention vastly improved recovery of DNA compared with the prior art methods. Furthermore, the present invention allows the treatment of smaller amounts of starting DNA compared with prior art methods thus providing more sensitive analysis of methylation of DNA.

Detection of Bisulphite Modified Vancomycin Resistant *Enterococci* spp (VRE) DNA Using Various Glass Beads Bisulphite Modification A 20 ul aliquot of VRE DNA (equivalent to $10^7$ cells) was denatured with 2.2 ul of 3M NaOH at 37° C. for 15 minutes. MethylEasy Xceed combined reagent 1 and 2 (220 ul) was added and the samples incubated at 80° C. for 1 hour and 30 minutes. Following incubation, magnetic beads (25 to 100 ul) of different properties were added. The beads were bound and washed as follows:

Silica, Magnetite Beads: Kisker Beads (Modified and Unmodified), MagSi (MagnaMedics) and Progentech Beads An aliquot of 6M GTC (240 ul) was added and the samples were allowed to bind at room temperature for 5 minutes. The samples were magnetized and supernatant discarded. The samples were then washed once with 400 ul of 3M NaCl and twice with 1 ml of 50% ethanol.

Beads with Switchable Surface Charge—Chargeswitch Beads (Invitrogen)

Beads with Switchable Surface Charge—CHARGESWITCH® Beads (Invitrogen)

An aliquot of 100 ul of kit-supplied binding buffer was added and the sample was allowed to bind at room temperature for 10 minutes. The samples were magnetized and supernatant discarded. The bead samples were washed once with 500 ul of wash buffer W13 and once with wash buffer W14.

Glass-Beads—Roche MAGNA PURE® Beads

An aliquot of 100 ul of kit-supplied binding buffer was added and the sample was allowed to bind at room temperature for 10 minutes. The samples were magnetized and supernatant discarded. The bead samples were washed once with an 800 ul aliquot of mix of 100% isopropanol/wash buffer 1 (1:1 ratio), once with 500 ul of wash buffer 1 and once with wash buffer 2.

Elution

An aliquot of 50 ul-100 ul of heated TE buffer, pH 11.5 was added to the beads and the samples incubated for 3 minutes at 80° C. The samples were then magnetised, and the eluate was transferred to new tubes. The elution step was repeated. The eluted DNA was washed and desulphonated by heating to 80 degrees for 23 minutes.

PCR Amplification and Detection of Sample

The eluted samples were amplified in a 25 ul reaction consisting 1× JumpStart pre-mixed master mix (Sigma, with 1.5 mM of $MgCl_2$ in a 1× reaction), 1 mM of $MgCl_2$ (the final $MgCl_2$ of 2.5 mM), 100 ng each of forward and reverse primer specific for detecting *Enterococcus* spp, and 3 ul each of 1$^{st}$ and 2$^{nd}$ elution. The samples were amplified at 95° C. for 3 minutes, 45 cycles of (95° C. 10 seconds, 48° C. 30 seconds, 68° C. 45 seconds) and 68° C. for 5 minutes.

Figure 8:
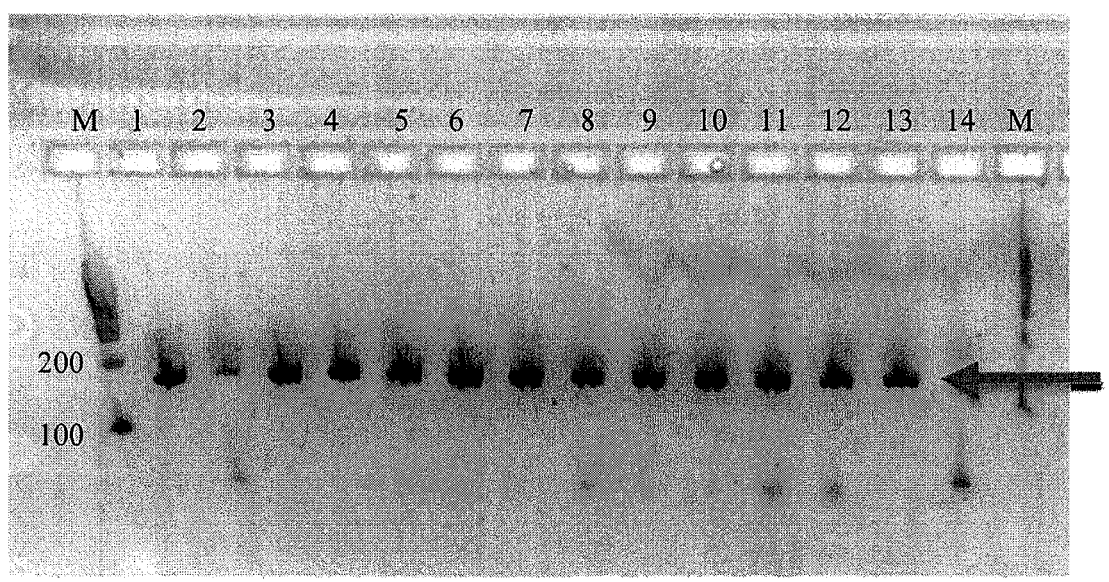
FIG. 8 shows PCR products generated from bisulphite modified VRE DNA after using various glass beads to remove the bisulphite and purify the converted DNA. Amplicon is indicated by the arrow.
Lane 1 Kisker beads, 50 ul
Lane 2 Kisker beads, pre-coupled with polyethyleneimine (25 kDa), 50 ul
Lane 3 Kisker beads, pre-coupled with poly-L-lysine, 50 ul
Lane 4 Kisker beads, pre-coupled with polyethylene glycol ether W-1 (Brij), 50 ul
Lane 5 MagSi beads, 50 ul
Lane 6 Progentech beads, 50 ul
Lane 7 CHARGESWITCH® beads, 25 ul
Lane 8 CHARGESWITCH® beads, 50 ul
Lane 9 CHARGESWITCH® beads, 100 ul
Lane 10 MAGNA PURE® beads, 25 ul
Lane 11 MAGNA PURE® beads, 50 ul
Lane 12 MAGNA PURE® beads, 100 ul
Lane 13 METHYLEASY™ Bisulphite Modification Kit modified VRE DNA
Lane 14 No Template control
Lane M HYPERLADDER™ IV molecular weight marker (Bioline)

The PCR products (15 μl) were then visualised on a pre-cast 4% E-gel (Invitrogen), as shown in FIG. 8.

Detection of Bisulphite Modified Methicillin Resistant *Staphylococcus aureus* (MRSA) DNA Using Silica-Magnetite Beads Bisulphite Modification Twenty microlitre aliquots of methicillin resistant *Staphylococcus aureus* (MRSA, Accrometrix Optiqual MRSA positive control) DNA (equivalent to 4000, 2000, 1000, 400, 200 and 0 cells) were denatured with 2.2 ul of 3M NaOH at 37° C. for 15 minutes. METHYLEASY™ Xceed combined reagents 1 and 2 (220 ul) was added and the samples were incubated at 80° C. for 20 minutes.

Following incubation, an aliquot of 25 ul magnetic beads (Progentech) was added to each reaction. The samples were allowed to bind at room temperature for 10 minutes. The samples were then magnetized and the supernatant discarded. The samples were then washed once with 600 ul of 3M NaCl and twice with 1 ml of 50% ethanol.

An aliquot of 25-30 ul of heated TE buffer, pH 11.5 was added to the beads and the samples desulphonated by incubated for 5 minutes at 80° C. The samples were then magnetised and the eluate transferred to new tubes.

PCR Amplification and Detection of Sample:

Three microlitre of the eluted samples were amplified in a 25 ul reaction consisting 1× FastStart pre-mixed master mix (Roche, with 2 mM of $MgCl_2$ in a 1× reaction), 1 mM of $MgCl_2$ (the final $MgCl_2$ of 3 mM) and 100 ng each of forward and reverse primer specific for detecting *Staphylococcus aureus*. The samples were amplified at 95° C. for 3 minutes, 50 cycles of (95° C. 10 seconds, 48° C. 30 seconds, 68° C. 45 seconds) and 68° C. for 5 minutes.

Figure 9:
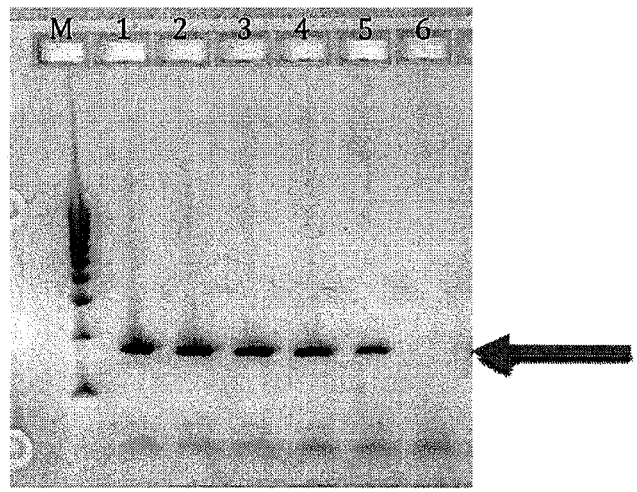
FIG. 9 shows PCR detection of bisulphite modified MRSA DNA using silica-magnetite beads to remove the bisulphite and purify the converted DNA. Amplicon is indicated by the arrow.
Lane 1 4000 cell equivalent (starting volume in the bisulphite modification)

The PCR products (15 μl) were then visualised on a pre-cast 2% E-gel (Invitrogen), as shown in FIG. 9.

Conversion of Human DNA Using Binding Columns to Remove the Bisulphite and Purify the Converted DNA One ng of human genomic DNA was diluted to a total volume of 20 ul with water and the DNA was denatured by adding 2.2 ul 3M NaOH and incubating for 15 mins at 37° C. METHYLEASY™ Xceed combined reagents 1+2 (220 ul) was added and the samples were incubated at 80° C. for 30 mins. The converted DNA was purified using a column (nano-purification, lot# 012705(VTS), P/N 4363246, L/N 0506002) by eluting using TE buffer, pH 11.5 and the eluate desulphonated by incubating at 95° C. for 30 mins.

To test for efficient conversion and de-sulphonation, a PCR amplification (nested PCR) was set-up for 24 genes, seeding 20 pg of converted DNA into each PCR. Results are shown in FIG. 10.

Similarly to the above, 0.5 ng (500 g DNA) was converted by sodium bisulphite and purified via a DNA binding column (ZYMO-SPIN I™). DNA was eluted in TE buffer pH 11.5, and desulphonated by incubating at 95° C. for 30 mins. PCR reactions were seeded with 20 pg converted DNA per PCR (nested PCR) in 24 different reactions, with the majority of PCRs producing an amplicon, as shown in FIG. 11.

To ensure that purification via solid support was still sensitive we repeated the above experiment (still using the ZYMO-SPIN I™ columns), however this time only 100 pg of DNA was used, equivalent to about 17 cells. After the DNA was converted, purified and desulphonated as above, 20 pg was seeded into 4 nested PCR reactions as shown in FIG. 12.

Conversion of Human DNA Using a High-Throughput 96 Well Purification Plate to Remove the Bisulphite and Purify the Converted DNA Male Human Genomic DNA (Promega Corporation #M7505 Madison, Wis. USA) was diluted to contain the following amounts in 20 μl of water (Sigma-Aldrich, # W4502 St Louis, Mo. USA); 1 μg, 100 ng, 25 ng, 1 ng. In a 96 well plate, 8 replicates for each DNA concentration were mixed with 2.2 μl of 3M sodium hydroxide made fresh using 0.1 g sodium hydroxide (Sigma-Aldrich, #S8045) in 830 μl of water. The plate was then sealed with adhesive PCR film (ABgene Epsom, UK) incubated at 37° for 15 minutes. A sodium bisulphite solution 2M, was made by adding 2.1 g of sodium metabisulphite (Merck # 1.06528.0500, Darmstadt, Germany) to a final volume of 5.5 ml which was pH adjusted to 5.0 with a sodium hydroxide solution. Two hundred and twenty microlitres of this solution was then added to each sample in the 96 well plate and mixed. The plate was resealed and incubated at 37° C. overnight (approx 16 hours).

Salmon Sperm DNA (Sigma-Adrich # D-9156) at a concentration of 1 μg/well was added to each well. 240 μl of a 5M Guanidinium Thiocyanate solution (Sigma-Aldrich # G9277) was added to each well, and the entire solution in each well was transferred to the corresponding well of a glass fibre DNA purification plate. The plate was then centrifuged at 1000×g for 4 minutes at room temperature, and the flow through collected in a waste tray. Each well of the purification plate was then washed with 800 μl of 80% isopropanol. The isopropanol was removed by centrifugation at 1000×g for 1 minute at room temperature. After discarding the flowthrough the centrifugation step was repeated for 2 minutes. The DNA was eluted from the purification plate into a PCR plate using 50 1l of a TE solution at pH 10.5. The modified DNA was desulphonated by incubating in a PCR machine at 95° C. for 30 minutes.

Nested PCR was performed to amplify a region within the ASC gene. Two microlitres of converted DNA was added to 12.5 μl 2× Master Mix (Promega #M7505), 100 ng of each of the forward and reverse primers, 8.5 μl water (Sigma-Aldrich). Cycling was performed in a Hybaid PX2 Thermal Cycler (ThermoFisher Scientific, Massachusetts USA) as follows; 95° C. for 3 minutes, then 30 cycles of 95 for 1 minute, 55° C. for 2 minutes, 72° C. for 2 minutes. The second round was performed under the same conditions, with 2 μl of the 1$^{st}$ round product used as template. The amplicons were visualised by electrophoresis using a 96 well egel (Invitrogen Corporation, California, USA, # G700802). Ten microlitres of each product was loaded into a well of the e-gel, which was then electrophoresed for 14 minutes, followed by visualisation using a UV transilluminator. The gel picture shown in FIG. 13 was formatted using Egel Editor Software (Invitrogen).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for treating nucleic acid comprising:

(a) providing an alkali environment to a nucleic acid sample;

(b) reacting the nucleic acid sample with a bisulphite reagent and incubating the reaction so as to form a treated nucleic acid sample;

(c) removing unwanted reagents or diluents from the treated nucleic acid sample; and (d) carrying out de-sulphonation of the treated nucleic acid at a temperature from 70° C. to 95° C. by adjusting the treated nucleic acid to a pH of between 10 and less than 12.5 to remove sulphonate groups present on the treated nucleic acid and obtain a nucleic acid sample substantially free of sulphonate groups.

2. The method according to claim 1, wherein more than 50% of the starting nucleic acid in the sample is retained.

3. The method according to claim 2, wherein more than 75% of the starting nucleic acid in the sample is retained.

4. The method according to claim 3, wherein more than 95% of the starting nucleic acid in the sample is retained.

5. The method according to claim 1, further comprising:
(e) processing or analysing the treated nucleic acid sample.

6. The method according to claim 1, wherein the sample comprises DNA, RNA, or both DNA and RNA.

7. The method according to claim 1, wherein the sample is prepared from a tissue, organ, cell, microorganism, biological sample, or environmental sample.

8. The method according to claim 7, wherein the tissue or organ is selected from the group consisting of brain, colon, urogenital, lung, renal, hematopoietic, breast, thymus, testis, ovary, uterus, and mixtures thereof.

9. The method according to claim 7, wherein the microorganism is selected from the group consisting of bacteria, virus, fungi, protozoan, viroid, and mixtures thereof.

10. The method according to claim 7, wherein the biological sample is selected from the group consisting of blood, urine, faeces, semen, cerebrospinal fluid, lavage, cells or tissue from brain, colon, urogenital, lung, renal, hematopoietic, breast, thymus, testis, ovary or uterus, tissues from embryonic or extra-embryonic lineages, environmental samples, plants, microorganisms, bacteria, intracellular parasites, viruses, fungi, protozoa, and viroids.

11. The method according to claim 1, wherein said method is carried out in a reaction vessel.

12. The method according to claim 11, wherein the reaction vessel is selected from the group consisting of a tube, plate, capillary tube, well, centrifuge tube, microfuge tube, slide, coverslip, and surface.

13. The method according to claim 1, wherein the bisulphite reagent is sodium metabisulphite.

14. The method according to claim 1, wherein the alkali environment is provided to the sample by adding an alkali reagent.

15. The method according to claim 14, wherein the alkali reagent is NaOH, KOH, or any compound that provides hydroxyl groups.

16. The method according to claim 1 wherein (a) is carried out in the presence of an additive capable of enhancing the bisulphite reaction.

17. The method according to claim 16 wherein the additive is selected from the group consisting of quinol, urea, methoxyamine, and mixtures thereof.

18. The method according to claim 1 wherein (b) results in any methylated cytosines in the nucleic acid sample remaining unchanged, while unmethylated cytosines are converted to uracils.

19. The method according to claim 1 wherein (d) is carried out by adjusting the pH of the treated nucleic acid with a buffer or alkali reagent.

20. The method according to claim 1, wherein the pH is adjusted to about 10.5.

21. The method according to claim 1 wherein (c) is carried out by immobilizing the treated nucleic acid on a solid support and washing unwanted reagents or diluents from the immobilized treated nucleic acid.

22. The method according to claim 21 wherein the solid support is glass, silica or ion-exchange media.

23. The method according to claim 22 wherein the solid support is a column, bead or magnetic bead.

24. The method according to claim 23 wherein the treated nucleic acid sample is eluted from the solid support prior to (d).

* * * * *

UNITED STATES PATENT AND TRADEMARK OFFICE
CERTIFICATE OF CORRECTION

PATENT NO.        : 8,168,777 B2
APPLICATION NO.   : 12/413380
DATED             : May 1, 2012
INVENTOR(S)       : Douglas Spencer Millar, Cassandra Jean Vockler and Neralie Ann Coulston It is certified that error appears in the above-identified patent and that said Letters Patent is hereby corrected as shown below:

At (Item 56), Page 2, Column 2, Line 42, Under Other Publications, change ""MethylLight:" to --"MethyLight:--.

At (Item 56), Page 2, Column 2, Lines 47-49, Under Other Publications, Below "695-696." delete "Frommer et al. "A genomic sequencing protocol that yields a positive display of 5-methylcytosine residues in individual DNA strands." Proc. Natl. Acad. Sci. 89:1827-1831.".

At (Item 56), Page 2, Column 2, Line 58, Under Other Publications, change "Briotechnology," to --Biotechnology,--.

At (Item 56), Page 3, Column 1, Line 10, Under Other Publications, change ""Epigentic" to --"Epigenetic--.

At (Item 56), Page 3, Column 1, Line 24, Under Other Publications, Below "2532-2534." delete "Database Accession No. M24485.".

At (Item 56), Page 3, Column 1, Line 35, Under Other Publications, change "Olignucleotides" to --Oligonucleotides--.

At (Item 56), Page 3, Column 2, Line 19, Under Other Publications, change "Vent$_R$®" to --VentR--.

At Column 8, Line 38 (Approx.), Change "ubiquination" to --ubiquitination--.
At Column 9, Line 58, Change "methyoxyamine" to --methoxyamine--.
At Column 12, Line 59, Change "(Kylsyth," to --(Kilsyth,--.
At Column 13, Line 35 (Approx.), Change "prepared," to --prepared--.
At Column 14, Line 26, Change "(R)," to --(R);--.
At Column 14, Line 67, After "required" insert --.--.
At Column 15, Line 46, After "DNA)" insert --.--.
At Column 16, Line 29, After "denaturation" insert --.--.

Signed and Sealed this
Eighteenth Day of December, 2012

David J. Kappos
*Director of the United States Patent and Trademark Office*

CERTIFICATE OF CORRECTION (continued)
U.S. Pat. No. 8,168,777 B2

At Column 16, Line 42, Change "AnalR" to --AnalaR--.

At Column 21, Line 7, After "1" insert --.--.

At Column 23, Line 6, Change "1) 8.06," to --1) 8.06--.

At Column 23, Line 18, Change "2=1.01" to --2=1.0 µl--.

At Column 23, Line 34 (Approx.), Change "C.×1.5°, 72° C.×1.5°," to --C.×1.5', 72° C.×1.5',--.

At Column 24, Lines 24-25, Below "ethanol." delete "Beads with Switchable Surface Charge-Chargeswitch Beads (Invitrogen)".

At Column 26, Line 16, Change "(Sigma-Adrich" to --(Sigma-Aldrich--.

At Column 26, Line 29 (Approx.), Change "5011" to --50 µl--.

At Column 26, Line 41 (Approx.), Change "egel" to --e-gel--.

At Column 26, Line 46 (Approx.), Change "Egel" to --E-gel--.